(12) United States Patent
Levine et al.

(10) Patent No.: US 7,601,692 B2
(45) Date of Patent: Oct. 13, 2009

(54) MCP-1 SPLICE VARIANTS AND METHODS OF USING SAME

(75) Inventors: Zurit Levine, Herzlia (IL); Amir Toporik, Azur (IL); Michal Ayalon-Soffer, Ramat-HaSharon (IL); Iris Hecht, Tel-Aviv (IL); Merav Beiman, Nes Ziona (IL); Dani Eshel, Karkur (IL); Tali Handelsman, Ramat-HaSharon (IL); Sarah Pollock, Tel-Aviv (IL)

(73) Assignee: Compugen Ltd., Tel Aviv (IL)

( * ) Notice: Subject to any disclaimer, the term of this patent is extended or adjusted under 35 U.S.C. 154(b) by 62 days.

(21) Appl. No.: 11/471,652

(22) Filed: Jun. 21, 2006

(65) Prior Publication Data

US 2007/0092484 A1    Apr. 26, 2007

Related U.S. Application Data

(63) Continuation-in-part of application No. 11/043,788, filed on Jan. 27, 2005, now abandoned, and a continuation-in-part of application No. 09/724,676, filed on Nov. 28, 2000, now abandoned.

(51) Int. Cl.
*A61K 38/19*    (2006.01)
*C07K 14/52*    (2006.01)

(52) U.S. Cl. .......................................... 514/12; 530/350
(58) Field of Classification Search .................. None
See application file for complete search history.

(56) References Cited

U.S. PATENT DOCUMENTS

2006/0014166 A1*    1/2006    Cohen et al. .................... 435/6

FOREIGN PATENT DOCUMENTS

WO    WO 2005/072049    *    8/2005

OTHER PUBLICATIONS

Beall et al., Journal of Biological Chemistry, 267(5):3455-3459, 1992.*
Gelfand et al. (1999) "ASDB: database of alternatively spliced genes" Nucl. Acids Res. 27:301-2.
Smith et al. (1989) "Alternative Splicing in the control of gene expression" Annu. Rev. Genet. 23:527-77.
Breibart et al. (1987) "Alternative Splicing: A ubiquitous mechanism for generation of multiple protein isoforms from single genes" Ann. Rev. Biochem. 56:467-495.
Chabot (1996) "Directing alternative splicing cast and scenarios" Trends Genet. 12:472-8.
Stamm et al. (1994) "A sequence compilation and comparison of exons that are alternatively spliced in neurons" Nucl. Acids Res. 22:1515-26.
Sharp (1994) "Split genes and RNA splicing" Cell 77:805-15.
Attwood, Science, vol. 290, pp. 1471-1473, 2000.
Lopez et al., Molecular Microbiology, vol. 32, pp. 886-891, 1999.
Gerhold et al., BioEssays, vol. 18, No. 12, pp. 973-981, 1996.
Wells et al., Journal of Leukocyte Biology, vol. 61, No. 5, pp. 545-550, 1997.
Hu et al., Genes & Development, 10:2251-2264, 1996.
Russell et al., Journal of Molecular Biology, vol. 244, pp. 332-350, 1994.

* cited by examiner

*Primary Examiner*—Marianne P Allen
(74) *Attorney, Agent, or Firm*—Fennemore Craig, P.C.

(57) ABSTRACT

Novel MCP-1 splice variant polypeptides and polynucleotides encoding same are provided. Also provided are pharmaceutical compositions comprising the splice variant polypeptides and polynucleotides, vectors and host cells comprising same. The compositions of the present invention are useful to treat various MCP-1 related disorders as well as for diagnosing, determining predisposition and/or prognosis of various disorders.

4 Claims, 6 Drawing Sheets

```
MCP1-65   1 MKVSAALLCLLLIAATFIPQGLAQPDAINAPVTCCYNFTNRKISVQRLAS 50
            ||||||||||||||||||||||||||||||||||||||||||||||||||
MCP1-WT   1 MKVSAALLCLLLIAATFIPQGLAQPDAINAPVTCCYNFTNRKISVQRLAS 50

MCP1-65  51 YRRITSSKCPKEAVM................................... 65
            |||||||||||||||
MCP1-WT  51 YRRITSSKCPKEAV.IFKTIVAKEICADPKQKWVQDSMDHLDKQTQTPKT 99
```

FIG. 1a

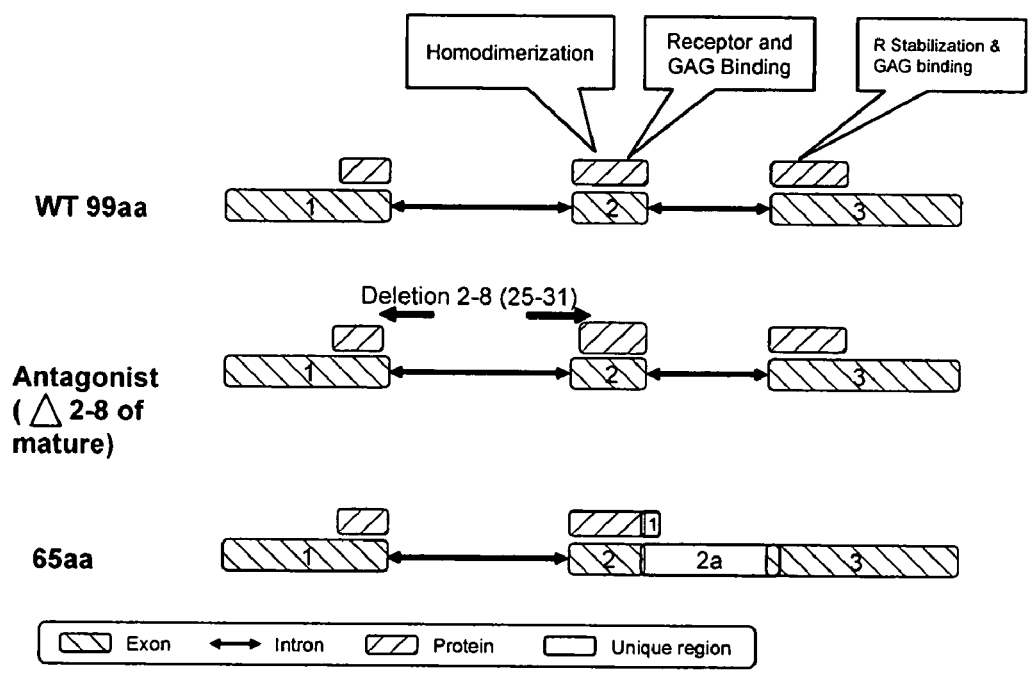

A. MCP1_99

GAATTCGCCACCATGAAAGTAAGCGCTGCCTTGCTTTGCCTCCTGCTGATCGCCGCGACA
TTCATTCCCCAGGGACTGGCCCAGCCAGATGCCATTAATGCCCCAGTGACTTGCTGTTAC
AACTTCACCAACCGCAAAATTAGTGTACAGAGGCTCGCTTCCTACCGCAGGATAACTAGT
TCTAAGTGCCCCAAAGAGGCAGTCATCTTCAAGACCATTGTGGCTAAGGAAATCTGCGCC
GACCCCAAGCAGAAGTGGGTCCAGGATTCTATGGACCACCTTGACAAACAGACCCAGACC
CCCAAGACTCCATGGTCACACCCCCAGTTTGAAAAGACCGGCCACCACCACCACCACCAC
CATCATGGCGGACAATGATGAGCGGCCGC

FIG. 2 (continued)

MKVSAALLCLLLIAATFIPQGLAQPDAINAPVTCCYNFTNRKISVQRLAS
YRRITSSKCPKEAVIFKTIVAKEICADPKQKWVQDSMDHLDKQTQTPKTP
WSHPQFEKTGHHHHHHHGGQ

B. MCP1_92 7ND

GAATTCGCCACCATGAAAGTGAGCGCTGCGCTGCTGTGCCTGCTTTTGATAGCTGCCACC
TTCATACCTCAAGGCTTGGCCCAGGTGACATGCTGCTATAACTTTACTAATAGAAAGATC
TCCGTGCAGCGGCTGGCTTCTTACCGGAGGATTACATCCTCCAAGTGTCCAAAAGAAGCC
GTGATCTTTAAGACCATAGTTGCCAAGGAGATATGCGCTGACCCCAAACAGAAATGGGTC
CAGGATAGCATGGATCACCTTGATAAACAGACTCAGACGCCTAAGACCCCATGGTCACAC
CCACAGTTCGAGAAGACAGGCCACCATCACCACCACCATCATCATGGCGGGCAATGATGA
GCGGCCGC

MKVSAALLCLLLIAATFIPQGLAQVTCCYNFTNRKISVQRLASYRRITSS
KCPKEAVIFKTIVAKEICADPKQKWVQDSMDHLDKQTQTPKTPWSHPQFE
KTGHHHHHHHGGQ

C. MCP1_65 Fc

GAATTCGCCACCATGAAAGTAAGCGCTGCCTTGCTTTGCCTCCTGCTGATCGCCGCGACAT
TCATTCCCCAGGGACTGGCCCAGCCAGATGCCATTAATGCCCCAGTGACTTGCTGTTACA
ACTTCACCAACCGCAAAATTAGTGTACAGAGGCTCGCTTCCTACCGCAGGATAACTAGTT
CTAAGTGCCCCAAAGAGGCAGTCATGGAGCCCAAGAGCTGTGACAAGACCCACACCTGCC
CCCCTTGCCCTGCCCCTGAGCTGCTGGGCGGACCCAGCGTGTTCCTGTTCCCTCCCAAGC
CTAAGGACACCCTGATGATCAGCAGAACCCCCGAGGTGACCTGTGTGGTGGTGGATGTGA
GCCACGAGGACCCTGAGGTGAAGTTCAACTGGTACGTGGACGGCGTGGAGGTGCACAATG
CCAAGACCAAGCCCAGGGAGGAGCAGTACGCCAGCACCTACCGGGTGGTGTCCGTGCTGA
CCGTGCTGCACCAGGATTGGCTGAACGGCAAGGAATACAAGTGTAAGGTGTCCAACAAGG
CCCTGCCTGCCCCTATCGAGAAAACCATCAGCAAGGCCAAGGGCCAGCCTAGGGAGCCCC
AGGTGTACACCCTGCCCCCTAGCAGAGATGAGCTGACCAAGAATCAGGTGTCCCTGACCT
GCCTGGTGAAGGGCTTCTACCCCAGCGACATCGCCGTGGAGTGGGAGAGCAACGGCCAGC
CCGAGAACAACTACAAGACCACCCCCCCTGTGCTGGACAGCGATGGCAGCTTCTTCCTGT
ACAGCAAGCTGACCGTGGATAAGAGCAGATGGCAGCAGGGCAACGTGTTCAGCTGCTCCG
TGATGCACGAGGCCCTGCACAATCACTACACCCAGAAGAGCCTGAGCCTGTCCCCTGGCA

FIG. 2 (continued)

AGTGATGAGCGGCCGC

MKVSAALLCLLLIAATFIPQGLAQPDAINAPVTCCYNFTNRKISVQRLAS
YRRITSSKCPKEAVMEPKSCDKTHTCPPCPAPELLGGPSVFLFPPKPKDT
LMISRTPEVTCVVVDVSHEDPEVKFNWYVDGVEVHNAKTKPREEQYASTY
RVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK

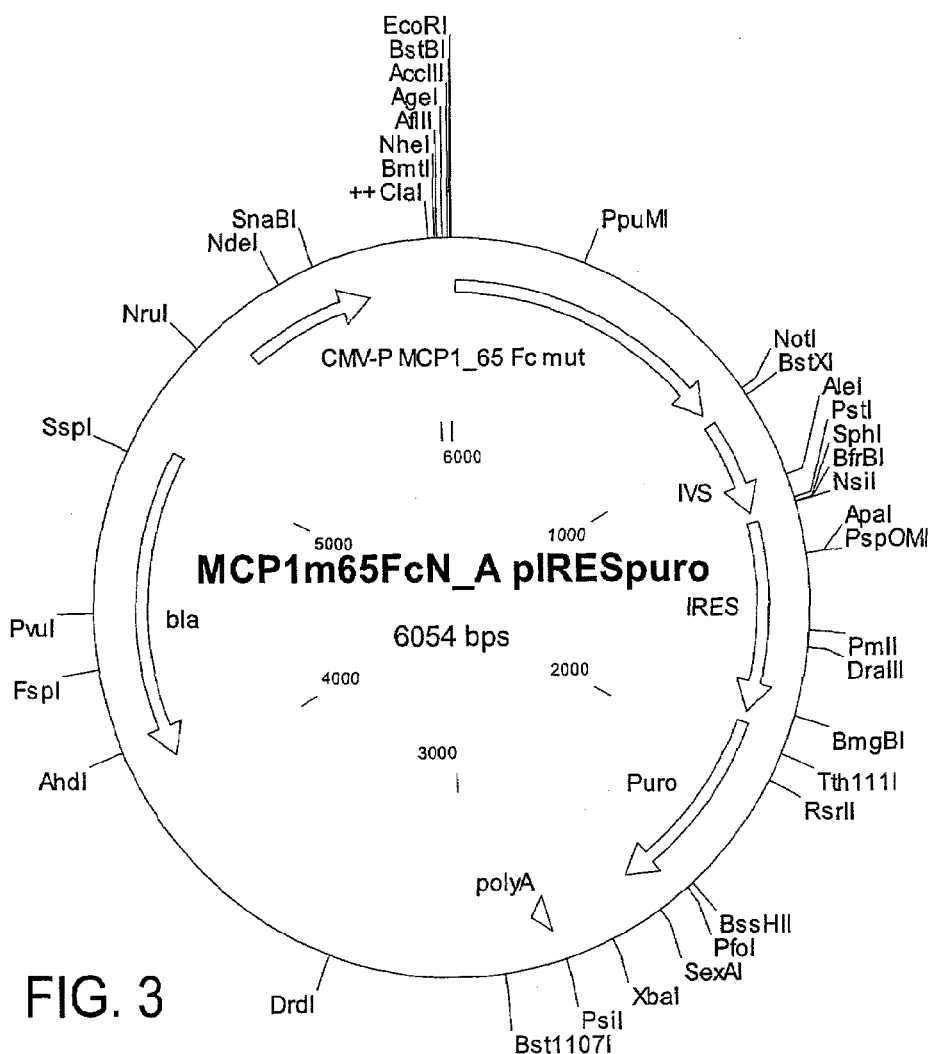

SEQUENCE LISTING

```
<160> NUMBER OF SEQ ID NOS: 35

<210> SEQ ID NO 1
<211> LENGTH: 1408
<212> TYPE: DNA
<213> ORGANISM: Homo sapiens

<400> SEQUENCE: 1
taaccctctt agttcacatc tgtggtcagt ctgggcttaa tggcacccca tcctccccat      60
ttgctcattt ggtctcagca gtgaatggaa aaagtgtctc gtcctgaccc cctgcttccc     120
tttcctactt cctggaaatc cacaggatgc tgcatttgct cagcagattt aacagcccac     180
ttatcactca tggaagatcc ctcctcctgc ttgactccgc cctctctccc tctgcccgct     240
ttcaataaga ggcagagaca gcagccagag gaaccgagag gctgagacta acccagaaac     300
atccaattct caaactgaag ctcgcactct cgcctccagc atgaaagtct ctgccgccct     360
tctgtgcctg ctgctcatag cagccacctt cattcccaa gggctcgctc agccagatgc     420
aatcaatgcc ccagtcacct gctgttataa cttcaccaat aggaagatct cagtgcagag     480
gctcgcgagc tatagaagaa tcaccagcag caagtgtccc aaagaagctg tgatgtgagt     540
tcagcacacc aaccttccct ggcctgaagt tcttccttgt ggagcaaggg acaagcctca     600
taaacctaga gtcagagagt gcactattta acttaatgta caaaggttcc caatgggaaa     660
actgaggcac caagggaaaa agtgaacccc aacatcactc tccacctggg tgcctattca     720
gaacacccca atttctttag cttgaagtca ggatggctcc acctggacac ctataggagc     780
agtttgccct gggttccctc cttccacctg cgttcctcct ctagctccca tggcagccct     840
ttggtgcaga atgggctgca cttctagacc aaaactgcaa aggaacttca tctaactctg     900
tcctccctcc ccacagcttc aagaccattg tggccaagga gatctgtgct gaccccaagc     960
agaagtgggt tcaggattcc atggaccacc tggacaagca aacccaaact ccgaagactt    1020
gaacactcac tccacaaccc aagaatctgc agctaactta ttttcccta gctttcccca    1080
```

```
gacaccctgt tttattttat tataatgaat tttgttgtt gatgtgaaac attatgcctt    1140
aagtaatgtt aattcttatt taagttattg atgttttaag tttatctttc atggtactag    1200
tgttttttag atacagagac ttggggaaat tgcttttcct cttgaaccac agttctaccc    1260
ctgggatgtt ttgagggtct ttgcaagaat cattaataca aagaattttt tttaacattc    1320
caatgcattg ctaaaatatt attgtggaaa tgaatatttt gtaactatta caccaaataa    1380 atatatttt gtacaaaacc tgacttcc                                        1408

<210> SEQ ID NO 2
<211> LENGTH: 387
<212> TYPE: DNA
<213> ORGANISM: Homo sapiens

<400> SEQUENCE: 2
taaccctctt agttcacatc tgtggtcagt ctgggcttaa tggcacccca tcctccccat      60
ttgctcattt ggtctcagca gtgaatggaa aaagtgtctc gtcctgaccc cctgcttccc     120
tttcctactt cctggaaatc acaggatgc tgcatttgct cagcagattt aacagcccac      180
ttatcactca tggaagatcc ctcctcctgc ttgactccgc cctctctccc tctgcccgct     240
ttcaataaga ggcagagaca gcagccagag gaaccgagag gctgagacta acccagaaac     300
atccaattct caaactgaag ctcgcactct cgcctccagc atgaaagtct ctgccgccct     360
tctgtgcctg ctgctcatag cagccac                                        387

<210> SEQ ID NO 3
<211> LENGTH: 382
<212> TYPE: DNA
<213> ORGANISM: Homo sapiens

<400> SEQUENCE: 3
gtgagttcag cacaccaacc ttccctggcc tgaagttctt ccttgtggag caagggacaa      60
gcctcataaa cctagagtca gagagtgcac tatttaactt aatgtacaaa ggttcccaat     120
gggaaaactg aggcaccaag ggaaaaagtg aacccaaca tcactctcca cctgggtgcc      180
tattcagaac accccaattt ctttagcttg aagtcaggat ggctccacct ggacacctat     240
aggagcagtt tgccctgggt tccctccttc cacctgcgtt cctcctctag ctcccatggc     300
agccctttgg tgcagaatgg gctgcacttc tagaccaaaa ctgcaaagga acttcatcta     360
actctgtcct ccctccccac ag                                             382

<210> SEQ ID NO 4
<211> LENGTH: 492
<212> TYPE: DNA
<213> ORGANISM: Homo sapiens

<400> SEQUENCE: 4
cttcaagacc attgtggcca aggagatctg tgctgacccc aagcagaagt gggttcagga      60
ttccatggac cacctggaca gcaaaccca actccgaag acttgaacac tcactccaca      120
acccaagaat ctgcagctaa cttatttcc cctagctttc cccagacacc ctgttttatt     180
ttattataat gaatttttgtt tgttgatgtg aaacattatg ccttaagtaa tgttaattct     240
tatttaagtt attgatgttt taagtttatc tttcatggta ctagtgtttt ttagatacag     300
agacttgggg aaattgcttt tcctcttgaa ccacagttct accctgggga tgttttgagg     360
gtctttgcaa gaatcattaa tacaaagaat ttttttaac attccaatgc attgctaaaa     420
```

```
tattattgtg gaaatgaata ttttgtaact attacaccaa ataaatatat ttttgtacaa      480
aacctgactt cc                                                          492
```

<210> SEQ ID NO 5
<211> LENGTH: 29
<212> TYPE: DNA
<213> ORGANISM: Homo sapiens

<400> SEQUENCE: 5

```
cttcattccc caagggctcg ctcagccag                                         29
```

<210> SEQ ID NO 6
<211> LENGTH: 118
<212> TYPE: DNA
<213> ORGANISM: Homo sapiens

<400> SEQUENCE: 6

```
atgcaatcaa tgccccagtc acctgctgtt ataacttcac caataggaag atctcagtgc       60
agaggctcgc gagctataga agaatcacca gcagcaagtg tcccaaagaa gctgtgat       118
```

<210> SEQ ID NO 7
<211> LENGTH: 99
<212> TYPE: PRT
<213> ORGANISM: Homo sapiens

<400> SEQUENCE: 7

```
Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr
```

<210> SEQ ID NO 8
<211> LENGTH: 99
<212> TYPE: PRT
<213> ORGANISM: Homo sapiens

<400> SEQUENCE: 8

```
Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80
```

Lys Trp Val Gln Asp Ser Met Asp His Leu Asp Lys Gln Thr Gln Thr
                85                  90                  95

Pro Lys Thr

<210> SEQ ID NO 9
<211> LENGTH: 65
<212> TYPE: PRT
<213> ORGANISM: Homo sapiens

<400> SEQUENCE: 9

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Met
65

<210> SEQ ID NO 10
<211> LENGTH: 389
<212> TYPE: DNA
<213> ORGANISM: Homo sapiens

<400> SEQUENCE: 10
gaattcgcca ccatgaaagt aagcgctgcc ttgctttgcc tcctgctgat cgccgcgaca      60
ttcattcccc agggactggc ccagccagat gccattaatg ccccagtgac ttgctgttac     120
aacttcacca accgcaaaat tagtgtacag aggctcgctt cctaccgcag ataactagt     180 tctaagtgcc ccaaagaggc agtcatcttc aagaccattg tggctaagga aatctgcgcc     240
gaccccaagc agaagtgggt ccaggattct atggaccacc ttgacaaaca gacccagacc     300
cccaagactc catggtcaca ccccagtttt gaaaagaccg ccaccacca ccaccaccac     360 catcatggcg acaatgatg agcggccgc                                          389

<210> SEQ ID NO 11
<211> LENGTH: 121
<212> TYPE: PRT
<213> ORGANISM: Homo sapiens

<400> SEQUENCE: 11

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

```
Pro Lys Thr Pro Trp Ser His Pro Gln Phe Glu Lys Thr Gly His His
            100                 105                 110
His His His His His His Gly Gly Gln
        115                 120

<210> SEQ ID NO 12
<211> LENGTH: 368
<212> TYPE: DNA
<213> ORGANISM: Homo sapiens

<400> SEQUENCE: 12
gaattcgcca ccatgaaagt gagcgctgcg ctgctgtgcc tgcttttgat agctgccacc      60 ttcataccctc aaggcttggc ccaggtgaca tgctgctata actttactaa tagaaagatc    120
tccgtgcagc ggctggcttc ttaccggagg attacatcct ccaagtgtcc aaaagaagcc    180
gtgatcttta agaccatagt tgccaaggag atatgcgctg accccaaaca gaaatgggtc    240
caggatagca tggatcacct tgataaacag actcagacgc ctaagacccc atggtcacac    300
ccacagttcg agaagacagg ccaccatcac caccaccatc atcatggcgg gcaatgatga    360
gcggccgc                                                              368

<210> SEQ ID NO 13
<211> LENGTH: 114
<212> TYPE: PRT
<213> ORGANISM: Homo sapiens

<400> SEQUENCE: 13

Met Lys Val Ser Ala Ala Leu Leu Cys Leu Leu Leu Ile Ala Ala Thr
1               5                   10                  15

Phe Ile Pro Gln Gly Leu Ala Gln Val Thr Cys Cys Tyr Asn Phe Thr
            20                  25                  30

Asn Arg Lys Ile Ser Val Gln Arg Leu Ala Ser Tyr Arg Arg Ile Thr
        35                  40                  45

Ser Ser Lys Cys Pro Lys Glu Ala Val Ile Phe Lys Thr Ile Val Ala
    50                  55                  60

Lys Glu Ile Cys Ala Asp Pro Lys Gln Lys Trp Val Gln Asp Ser Met
65                  70                  75                  80

Asp His Leu Asp Lys Gln Thr Gln Thr Pro Lys Thr Pro Trp Ser His
                85                  90                  95

Pro Gln Phe Glu Lys Thr Gly His His His His His His Gly
            100                 105                 110

Gly Gln

<210> SEQ ID NO 14
<211> LENGTH: 917
<212> TYPE: DNA
<213> ORGANISM: Homo sapiens

<400> SEQUENCE: 14
gaattcgcca ccatgaaagt aagcgctgcc ttgctttgcc tcctgctgat cgccgcgaca      60
ttcattcccc agggactggc ccagccagat gccattaatg ccccagtgac ttgctgttac    120
aacttcacca accgcaaaat tagtgtacag aggctcgctt cctaccgcag ataactagt    180 tctaagtgcc ccaaagaggc agtcatggag cccaagagct gtgacaagac ccacacctgc    240 ccccttgcc ctgcccctga gctgctgggc ggacccagtg tgttcctgtt ccctcccaag    300
cctaaggaca ccctgatgat cagcagaacc cccgaggtga cctgtgtggt ggtggatgtg    360
```

-continued

```
agccacgagg accctgaggt gaagttcaac tggtacgtgg acggcgtgga ggtgcacaat    420
gccaagacca agcccaggga ggagcagtac gccagcacct accgggtggt gtccgtgctg    480
accgtgctgc accaggattg gctgaacggc aaggaataca agtgtaaggt gtccaacaag    540
gccctgcctg cccctatcga aaaaccatc agcaaggcca agggccagcc tagggagccc    600
caggtgtaca ccctgccccc tagcagagat gagctgacca gaatcaggt gtccctgacc      660
tgcctggtga agggcttcta ccccagcgac atcgccgtgg agtgggagag caacggccag    720
cccgagaaca actacaagac cacccccct gtgctggaca gcgatggcag cttcttcctg      780
tacagcaagc tgaccgtgga taagagcaga tggcagcagg gcaacgtgtt cagctgctcc    840
gtgatgcacg aggccctgca caatcactac acccagaaga gcctgagcct gtcccctggc    900
aagtgatgag cggccgc                                                    917
```

<210> SEQ ID NO 15
<211> LENGTH: 297
<212> TYPE: PRT
<213> ORGANISM: Homo sapiens

<400> SEQUENCE: 15

```
Met Lys Val Ser Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
                20                  25                  30

Thr Cys Cys Tyr Asn Phe Thr Asn Arg Lys Ile Ser Val Gln Arg Leu
            35                  40                  45

Ala Ser Tyr Arg Arg Ile Thr Ser Ser Lys Cys Pro Lys Glu Ala Val
        50                  55                  60

Met Glu Pro Lys Ser Cys Asp Lys Thr His Thr Cys Pro Pro Cys Pro
65                  70                  75                  80

Ala Pro Glu Leu Leu Gly Gly Pro Ser Val Phe Leu Phe Pro Pro Lys
                85                  90                  95

Pro Lys Asp Thr Leu Met Ile Ser Arg Thr Pro Glu Val Thr Cys Val
            100                 105                 110

Val Val Asp Val Ser His Glu Asp Pro Glu Val Lys Phe Asn Trp Tyr
        115                 120                 125

Val Asp Gly Val Glu Val His Asn Ala Lys Thr Lys Pro Arg Glu Glu
    130                 135                 140

Gln Tyr Ala Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
            180                 185                 190

Pro Arg Glu Pro Gln Val Tyr Thr Leu Pro Pro Ser Arg Asp Glu Leu
        195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Lys Leu Thr Val Asp Lys Ser Arg Trp Gln Gln Gly Asn Val
            260                 265                 270
```

Phe Ser Cys Ser Val Met His Glu Ala Leu His Asn His Tyr Thr Gln
            275                 280                 285

Lys Ser Leu Ser Leu Ser Pro Gly Lys
    290                 295

<210> SEQ ID NO 16
<211> LENGTH: 20
<212> TYPE: DNA
<213> ORGANISM: Homo sapiens

<400> SEQUENCE: 16
cttagcgcag aagtcatgcc                                               20

<210> SEQ ID NO 17
<211> LENGTH: 59
<212> TYPE: DNA
<213> ORGANISM: Homo sapiens

<400> SEQUENCE: 17
ggataactag ttctaagtgc cccaaagagg cagtcatgga gcccaagagc tgtgacaag   59

<210> SEQ ID NO 18
<211> LENGTH: 713
<212> TYPE: DNA
<213> ORGANISM: Homo sapiens

<400> SEQUENCE: 18
ttcgaaccca agagctgtga caagacccac acctgccccc cttgccctgc ccctgagctg    60
ctgggcggac ccagcgtgtt cctgttccct cccaagccta aggacaccct gatgatcagc   120 agaaccccccg aggtgacctg tgtggtggtg gatgtgagcc acgaggaccc tgaggtgaag   180
ttcaactggt acgtggacgg cgtggaggtg cacaatgcca agaccaagcc cagggaggag   240
cagtacgcca gcacctaccg ggtggtgtcc gtgctgaccg tgctgcacca ggattggctg   300
aacggcaagg aatacaagtg taaggtgtcc aacaaggccc tgcctgcccc tatcgagaaa   360
accatcagca aggccaaggg ccagcctagg gagccccagg tgtacaccct gccccctagc   420
agagatgagc tgaccaagaa tcaggtgtcc ctgacctgcc tggtgaaggg cttctacccc   480
agcgacatcg ccgtggagtg ggagagcaac ggccagcccg agaacaacta caagaccacc   540 cccctgtgc tggacagcga tggcagcttc ttcctgtaca gcaagctgac cgtggataag   600
agcagatggc agcagggcaa cgtgttcagc tgctccgtga tgcacgaggc cctgcacaat   660
cactacaccc agaagagcct gagcctgtcc cctggcaagt gatgagcggc cgc         713

<210> SEQ ID NO 19
<211> LENGTH: 232
<212> TYPE: PRT
<213> ORGANISM: Homo sapiens

<400> SEQUENCE: 19

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

-continued

```
Asp Gly Val Glu Val His Asn Ala Lys Thr Lys Pro Arg Glu Glu Gln
 65                  70                  75                  80

Tyr Ala Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 20
<211> LENGTH: 65
<212> TYPE: PRT
<213> ORGANISM: Homo sapiens

<400> SEQUENCE: 20

Met Lys Val Ser Ala Ala Leu Leu Cys Leu Leu Leu Ile Ala Ala Thr
  1               5                  10                  15

Phe Ile Pro Gln Gly Leu Ala Gln Pro Asp Ala Ile Asn Ala Pro Val
                 20                  25                  30

Thr Cys Cys Tyr Asn Phe Thr Asn Arg Lys Ile Ser Val Gln Arg Leu
            35                  40                  45

Ala Ser Leu Arg Val Ile Thr Ser Ser Lys Cys Pro Lys Glu Ala Val
        50                  55                  60

Met
 65

<210> SEQ ID NO 21
<211> LENGTH: 297
<212> TYPE: PRT
<213> ORGANISM: Homo sapiens

<400> SEQUENCE: 21

Met Lys Val Ser Ala Ala Leu Leu Cys Leu Leu Leu Ile Ala Ala Thr
  1               5                  10                  15

Phe Ile Pro Gln Gly Leu Ala Gln Pro Asp Ala Ile Asn Ala Pro Val
                 20                  25                  30

Thr Cys Cys Tyr Asn Phe Thr Asn Arg Lys Ile Ser Val Gln Arg Leu
            35                  40                  45

Ala Ser Leu Arg Val Ile Thr Ser Ser Lys Cys Pro Lys Glu Ala Val
        50                  55                  60

Met Glu Pro Lys Ser Cys Asp Lys Thr His Thr Cys Pro Pro Cys Pro
 65                  70                  75                  80
```

```
Ala Pro Glu Leu Leu Gly Gly Pro Ser Val Phe Leu Phe Pro Pro Lys
                85                  90                  95
Pro Lys Asp Thr Leu Met Ile Ser Arg Thr Pro Glu Val Thr Cys Val
            100                 105                 110
Val Val Asp Val Ser His Glu Asp Pro Glu Val Lys Phe Asn Trp Tyr
        115                 120                 125
Val Asp Gly Val Glu Val His Asn Ala Lys Thr Lys Pro Arg Glu Glu
    130                 135                 140
Gln Tyr Ala Ser Thr Tyr Arg Val Val Ser Val Leu Thr Val Leu His
145                 150                 155                 160
Gln Asp Trp Leu Asn Gly Lys Glu Tyr Lys Cys Lys Val Ser Asn Lys
                165                 170                 175
Ala Leu Pro Ala Pro Ile Glu Lys Thr Ile Ser Lys Ala Lys Gly Gln
            180                 185                 190
Pro Arg Glu Pro Gln Val Tyr Thr Leu Pro Pro Ser Arg Asp Glu Leu
        195                 200                 205
Thr Lys Asn Gln Val Ser Leu Thr Cys Leu Val Lys Gly Phe Tyr Pro
    210                 215                 220
Ser Asp Ile Ala Val Glu Trp Glu Ser Asn Gly Gln Pro Glu Asn Asn
225                 230                 235                 240
Tyr Lys Thr Thr Pro Pro Val Leu Asp Ser Asp Gly Ser Phe Phe Leu
                245                 250                 255
Tyr Ser Lys Leu Thr Val Asp Lys Ser Arg Trp Gln Gln Gly Asn Val
            260                 265                 270
Phe Ser Cys Ser Val Met His Glu Ala Leu His Asn His Tyr Thr Gln
        275                 280                 285
Lys Ser Leu Ser Leu Ser Pro Gly Lys
    290                 295

<210> SEQ ID NO 22
<211> LENGTH: 221
<212> TYPE: DNA
<213> ORGANISM: Homo sapiens

<400> SEQUENCE: 22
gaattcgcca ccatgaaagt aagcgctgcc ttgctttgcc tcctgctgat cgccgcgaca    60
ttcattcccc agggactggc ccagccagat gccattaatg ccccagtgac ttgctgttac   120
aacttcacca accgcaaaat tagtgtacag aggctcgctt ccctgcgcgt gataactagt   180
tctaagtgcc ccaaagaggc agtcatgtga tgagcggccg c                       221

<210> SEQ ID NO 23
<211> LENGTH: 917
<212> TYPE: DNA
<213> ORGANISM: Homo sapiens

<400> SEQUENCE: 23
gaattcgcca ccatgaaagt aagcgctgcc ttgctttgcc tcctgctgat cgccgcgaca    60
ttcattcccc agggactggc ccagccagat gccattaatg ccccagtgac ttgctgttac   120
aacttcacca accgcaaaat tagtgtacag aggctcgctt ccctgcgcgt gataactagt   180
tctaagtgcc ccaaagaggc agtcatggag cccaagagct gtgacaagac ccacacctgc   240
cccccttgcc ctgcccctga gctgctgggc ggaccccagc gtgttcctgt tcctcccaag   300
cctaaggaca cctgatgat cagcagaacc ccgaggtga cctgtgtggt ggtggatgtg   360
agccacgagg accctgaggt gaagttcaac tggtacgtgg acggcgtgga ggtgcacaat   420
```

```
gccaagacca agcccaggga ggagcagtac gccagcacct accgggtggt gtccgtgctg      480
accgtgctgc accaggattg gctgaacggc aaggaataca agtgtaaggt gtccaacaag      540
gccctgcctg ccctatcga gaaaaccatc agcaaggcca agggccagcc tagggagccc      600
caggtgtaca ccctgccccc tagcagagat gagctgacca gaatcaggt gtccctgacc      660 tgcctggtga agggcttcta ccccagcgac atcgccgtgg agtgggagag caacggccag      720
cccgagaaca actacaagac cacccccct gtgctggaca cgatggcag cttcttcctg       780 tacagcaagc tgaccgtgga taagagcaga tggcagcagg gcaacgtgtt cagctgctcc     840
gtgatgcacg aggccctgca caatcactac acccagaaga gcctgagcct gtcccctggc     900
aagtgatgag cggccgc                                                   917

<210> SEQ ID NO 24
<211> LENGTH: 279
<212> TYPE: DNA
<213> ORGANISM: Homo sapiens

<400> SEQUENCE: 24
atgaaagtct ctgccgccct tctgtgcctg ctgctcatag cagccacctt cattccccaa      60
gggctcgctc aggtcacctg ctgttataac ttcaccaata ggaagatctc agtgcagagg     120
ctcgcgagct atagaagaat caccagcagc aagtgtccca agaagctgt gatcttcaag      180 accattgtgg ccaaggagat ctgtgctgac cccaagcaga agtgggttca ggattccatg     240
gaccacctgg acaagcaaac ccaaactccg aagacttga                           279

<210> SEQ ID NO 25
<211> LENGTH: 92
<212> TYPE: PRT
<213> ORGANISM: Homo sapiens

<400> SEQUENCE: 25

Met Lys Val Ser Ala Ala Leu Leu Cys Leu Leu Leu Ile Ala Ala Thr
1               5                   10                  15

Phe Ile Pro Gln Gly Leu Ala Gln Val Thr Cys Cys Tyr Asn Phe Thr
            20                  25                  30

Asn Arg Lys Ile Ser Val Gln Arg Leu Ala Ser Tyr Arg Arg Ile Thr
        35                  40                  45

Ser Ser Lys Cys Pro Lys Glu Ala Val Ile Phe Lys Thr Ile Val Ala
    50                  55                  60

Lys Glu Ile Cys Ala Asp Pro Lys Gln Lys Trp Val Gln Asp Ser Met
65                  70                  75                  80

Asp His Leu Asp Lys Gln Thr Gln Thr Pro Lys Thr
                85                  90

<210> SEQ ID NO 26
<211> LENGTH: 65
<212> TYPE: PRT
<213> ORGANISM: Homo sapiens

<400> SEQUENCE: 26

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45
```

Ala Ser Leu Arg Arg Ile Thr Ser Ser Lys Cys Pro Lys Glu Ala Val
    50                  55                  60

Met
65

<210> SEQ ID NO 27
<211> LENGTH: 198
<212> TYPE: DNA
<213> ORGANISM: Homo sapiens

<400> SEQUENCE: 27
atgaaagtct ctgccgccct tctgtgcctg ctgctcatag cagccacctt cattccccaa      60
gggctcgctc agccagatgc aatcaatgcc ccagtcacct gctgttataa cttcaccaat     120
aggaagatct cagtgcagag gctcgcgagc ttgagaagaa tcaccagcag caagtgtccc     180
aaagaagctg tgatgtga                                                   198

<210> SEQ ID NO 28
<211> LENGTH: 65
<212> TYPE: PRT
<213> ORGANISM: Homo sapiens

<400> SEQUENCE: 28

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
                20                  25                  30

Thr Cys Cys Tyr Asn Phe Thr Asn Arg Lys Ile Ser Val Gln Arg Leu
            35                  40                  45

Ala Ser Tyr Arg Val Ile Thr Ser Ser Lys Cys Pro Lys Glu Ala Val
    50                  55                  60

Met
65

<210> SEQ ID NO 29
<211> LENGTH: 198
<212> TYPE: DNA
<213> ORGANISM: Homo sapiens

<400> SEQUENCE: 29
atgaaagtct ctgccgccct tctgtgcctg ctgctcatag cagccacctt cattccccaa      60
gggctcgctc agccagatgc aatcaatgcc ccagtcacct gctgttataa cttcaccaat     120
aggaagatct cagtgcagag gctcgcgagc tatagagtaa tcaccagcag caagtgtccc     180
aaagaagctg tgatgtga                                                   198

<210> SEQ ID NO 30
<211> LENGTH: 297
<212> TYPE: PRT
<213> ORGANISM: Homo sapiens

<400> SEQUENCE: 30

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
                20                  25                  30

Thr Cys Cys Tyr Asn Phe Thr Asn Arg Lys Ile Ser Val Gln Arg Leu
            35                  40                  45

-continued

```
Ala Ser Leu Arg Arg Ile Thr Ser Ser Lys Cys Pro Lys Glu Ala Val
     50                  55                  60
Met Glu Pro Lys Ser Cys Asp Lys Thr His Thr Cys Pro Pro Cys Pro
 65                  70                  75                  80
Ala Pro Glu Leu Leu Gly Gly Pro Ser Val Phe Leu Phe Pro Pro Lys
                 85                  90                  95
Pro Lys Asp Thr Leu Met Ile Ser Arg Thr Pro Glu Val Thr Cys Val
            100                 105                 110
Val Val Asp Val Ser His Glu Asp Pro Glu Val Lys Phe Asn Trp Tyr
        115                 120                 125
Val Asp Gly Val Glu Val His Asn Ala Lys Thr Lys Pro Arg Glu Glu
130                 135                 140
Gln Tyr Ala Ser Thr Tyr Arg Val Val Ser Val Leu Thr Val Leu His
145                 150                 155                 160
Gln Asp Trp Leu Asn Gly Lys Glu Tyr Lys Cys Lys Val Ser Asn Lys
                165                 170                 175
Ala Leu Pro Ala Pro Ile Glu Lys Thr Ile Ser Lys Ala Lys Gly Gln
            180                 185                 190
Pro Arg Glu Pro Gln Val Tyr Thr Leu Pro Pro Ser Arg Asp Glu Leu
        195                 200                 205
Thr Lys Asn Gln Val Ser Leu Thr Cys Leu Val Lys Gly Phe Tyr Pro
210                 215                 220
Ser Asp Ile Ala Val Glu Trp Glu Ser Asn Gly Gln Pro Glu Asn Asn
225                 230                 235                 240
Tyr Lys Thr Thr Pro Pro Val Leu Asp Ser Asp Gly Ser Phe Phe Leu
                245                 250                 255
Tyr Ser Lys Leu Thr Val Asp Lys Ser Arg Trp Gln Gln Gly Asn Val
            260                 265                 270
Phe Ser Cys Ser Val Met His Glu Ala Leu His Asn His Tyr Thr Gln
        275                 280                 285
Lys Ser Leu Ser Leu Ser Pro Gly Lys
290                 295
```

<210> SEQ ID NO 31
<211> LENGTH: 917
<212> TYPE: DNA
<213> ORGANISM: Homo sapiens

<400> SEQUENCE: 31

```
gaattcgcca ccatgaaagt aagcgctgcc ttgctttgcc tcctgctgat cgccgcgaca    60
ttcattcccc agggactggc ccagccagat gccattaatg ccccagtgac ttgctgttac   120
aacttcacca accgcaaaat tagtgtacag aggctcgctt ccctgcgcag ataactagt   180
tctaagtgcc ccaaagaggc agtcatggag cccaagagct gtgacaagac ccacacctgc   240
cccccttgcc ctgcccctga gctgctgggc ggacccagtg tgttcctgtt ccctcccaag   300
cctaaggaca ccctgatgat cagcagaacc cccgaggtga cctgtgtggt ggtggatgtg   360
agccacgagg accctgaggt gaagttcaac tggtacgtgg acggcgtgga ggtgcacaat   420
gccaagacca gcccagggga ggagcagtac gccagcacct accgggtggt gtccgtgctg   480
accgtgctgc accaggattg gctgaacggc aaggaataca agtgtaaggt gtccaacaag   540
gccctgcctg cccctatcga gaaaaccatc agcaaggcca agggccagcc tagggagccc   600
caggtgtaca ccctgccccc tagcagagat gagctgacca gaatcaggt gtccctgacc   660
tgcctggtga agggcttcta ccccagcgac atcgccgtgg agtgggagag caacggccag   720
```

```
cccgagaaca actacaagac cacccccct gtgctggaca gcgatggcag cttcttcctg      780
tacagcaagc tgaccgtgga taagagcaga tggcagcagg gcaacgtgtt cagctgctcc      840
gtgatgcacg aggccctgca caatcactac acccagaaga gcctgagcct gtcccctggc      900
aagtgatgag cggccgc                                                      917

<210> SEQ ID NO 32
<211> LENGTH: 297
<212> TYPE: PRT
<213> ORGANISM: Homo sapiens

<400> SEQUENCE: 32

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
                20                  25                  30

Thr Cys Cys Tyr Asn Phe Thr Asn Arg Lys Ile Ser Val Gln Arg Leu
            35                  40                  45

Ala Ser Tyr Arg Val Ile Thr Ser Ser Lys Cys Pro Lys Glu Ala Val
        50                  55                  60

Met Glu Pro Lys Ser Cys Asp Lys Thr His Thr Cys Pro Pro Cys Pro
65                  70                  75                  80

Ala Pro Glu Leu Leu Gly Gly Pro Ser Val Phe Leu Phe Pro Pro Lys
                85                  90                  95

Pro Lys Asp Thr Leu Met Ile Ser Arg Thr Pro Glu Val Thr Cys Val
                100                 105                 110

Val Val Asp Val Ser His Glu Asp Pro Glu Val Lys Phe Asn Trp Tyr
            115                 120                 125

Val Asp Gly Val Glu Val His Asn Ala Lys Thr Lys Pro Arg Glu Glu
        130                 135                 140

Gln Tyr Ala Ser Thr Tyr Arg Val Val Ser Val Leu Thr Val Leu His
145                 150                 155                 160

Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
                180                 185                 190

Pro Arg Glu Pro Gln Val Tyr Thr Leu Pro Pro Ser Arg Asp Glu Leu
            195                 200                 205

Thr Lys Asn Gln Val Ser Leu Thr Cys Leu Val Lys Gly Phe Tyr Pro
        210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Lys Leu Thr Val Asp Lys Ser Arg Trp Gln Gln Gly Asn Val
                260                 265                 270

Phe Ser Cys Ser Val Met His Glu Ala Leu His Asn His Tyr Thr Gln
            275                 280                 285

Lys Ser Leu Ser Leu Ser Pro Gly Lys
        290                 295

<210> SEQ ID NO 33
<211> LENGTH: 917
<212> TYPE: DNA
<213> ORGANISM: Homo sapiens
```

```
<400> SEQUENCE: 33
gaattcgcca ccatgaaagt aagcgctgcc ttgctttgcc tcctgctgat cgccgcgaca      60
ttcattcccc agggactggc ccagccagat gccattaatg ccccagtgac ttgctgttac     120
aacttcacca accgcaaaat tagtgtacag aggctcgctt cctaccgcgt gataactagt     180
tctaagtgcc ccaaagaggc agtcatggag cccaagagct gtgacaagac ccacacctgc     240
cccccttgcc ctgcccctga gctgctgggc ggacccagcg tgttcctgtt ccctcccaag     300
cctaaggaca ccctgatgat cagcagaacc cccgaggtga cctgtgtggt ggtggatgtg     360
agccacgagg accctgaggt gaagttcaac tggtacgtgg acggcgtgga ggtgcacaat     420
gccaagacca gcccagggga ggagcagtac gccagcacct accgggtggt gtccgtgctg     480
accgtgctgc accaggattg gctgaacggc aaggaataca agtgtaaggt gtccaacaag     540
gccctgcctg cccctatcga gaaaaccatc agcaaggcca agggccagcc tagggagccc     600
caggtgtaca ccctgccccc tagcagagat gagctgacca gaatcaggt gtccctgacc      660
tgcctggtga agggcttcta ccccagcgac atcgccgtgg agtgggagag caacggccag     720
cccgagaaca actacaagac cacccccccct gtgctggaca gcgatggcag cttcttcctg    780
tacagcaagc tgaccgtgga taagagcaga tggcagcagg gcaacgtgtt cagctgctcc     840
gtgatgcacg aggccctgca caatcactac acccagaaga gcctgagcct gtccctggc      900
aagtgatgag cggccgc                                                    917

<210> SEQ ID NO 34
<211> LENGTH: 198
<212> TYPE: DNA
<213> ORGANISM: Homo sapiens

<400> SEQUENCE: 34
atgaaagtct ctgccgccct tctgtgcctg ctgctcatag cagccacctt cattccccaa      60
gggctcgctc agccagatgc aatcaatgcc ccagtcacct gctgttataa cttcaccaat     120
aggaagatct cagtgcagag gctcgcgagc ttgagagtaa tcaccagcag caagtgtccc     180
aaagaagctg tgatgtga                                                   198

<210> SEQ ID NO 35
<211> LENGTH: 42
<212> TYPE: PRT
<213> ORGANISM: Homo sapiens

<400> SEQUENCE: 35

Gln Pro Asp Ala Ile Asn Ala Pro Val Thr Cys Cys Tyr Asn Phe Thr
1               5                   10                  15
Asn Arg Lys Ile Ser Val Gln Arg Leu Ala Ser Tyr Arg Arg Ile Thr
            20                  25                  30
Ser Ser Lys Cys Pro Lys Glu Ala Val Met
        35                  40
```

MCP-1 SPLICE VARIANTS AND METHODS OF USING SAME

CROSS-REFERENCE TO RELATED APPLICATIONS

This application is a continuation in part of U.S. patent application Ser. No. 09/724,676 filed Nov. 28, 2000 now abandoned, and U.S. patent application Ser. No. 11/043,788 filed Jan. 27, 2005 now abandoned, the disclosures of which are incorporated herein by reference.

FIELD OF THE INVENTION

The present invention relates to novel MCP-1 splice variant polypeptides, and polynucleotides encoding same, vectors and host cells comprising same and more particularly, to therapeutic and diagnostic compositions and methods utilizing same.

BACKGROUND OF THE INVENTION

CCL2, also known as Monocyte Chemoattractant Protein 1 (MCP-1), belongs to the CC chemokine family, which is characterized by the ability to attract mononuclear cells to sites of chronic inflammation. CCL2 is a potent chemoattractant of monocytes, and this seems to be its predominant physiological role. CCL2 has also been shown to attract dendritic and memory T cells, as well as basophils, and stimulate histamine release from the latter (Rollins, 1996, Mol Med Today. 2:198).

CCL2 is thought to play a critical role in inflammatory diseases that involve mononuclear cell infiltration, such as atherosclerosis, rheumatoid arthritis and multiple sclerosis. Furthermore, this chemokine has also been implicated in inflammation of the nervous system and other diseases and conditions, both with and without an obvious inflammatory component including atopic dermatitis, renal disease, pleurisy, allergic inflammation and asthma, colitis, endometriosis, polymyositis and dermatomyositis, uveitis, and various vascular disorders (such as atherosclerosis, restenosis after coronary intervention, intimal hyperplasia, arteriogenesis, ischemia and stroke) and even in the control of leptin secretion and hence, obesity and cachexia (Rollins, 1996, Mol Med Today. 2:198; Dawson et al., 2003, Expert Opin Ther Targets. 7:35; Daly and Rollins, 2003, Microcir. 10: 247; Charo and Taubman, 2004, Circ Res. 95: 858)

The cognate receptor for CCL2 is the seven-transmembrane-spanning G-protein-coupled receptor CCR2. The two isoforms of this receptor are CCR2A and CCR2B, which differ in their signaling C-terminal regions. The CCR2B isoform is more abundantly expressed on monocytes, and is probably the primary mediator of monocyte responses to CCL2 during inflammation (Tanaka et al, 2002, Biochem Biophys Res Commun. 290: 73). In addition to its interaction with CCR2, CCL2 binds to glycosaminoglycan (GAG) and form oligomers which are essential for its in vivo function. Binding to the GAG chains of cell surface proteoglycans is thought to facilitate the formation of high-localized concentrations of chemokines, which in turn provide directional signals for leukocyte migration (Proudfoot, A. E., et al., 2003, Proc Natl Acad Sci USA. 100:1885; Lau, E. K., et al., 2004, J Biol Chem. 279:22294).

The expression of CCL2 can be induced in various tissues in response to different types of inflammatory lesions. CCL2 mediates the influx of inflammatory macrophages, derived from peripheral blood monocytes, into the sites of injury. These macrophages secrete proinflammatory cytokines, tissue degrading enzymes and chemokines that mediate the influx of other inflammatory cells, leading to tissue destruction in chronic inflammatory diseases. This suggests that inhibition of monocyte migration into inflammatory lesions might be an effective mechanism to modulate disease progression in chronic inflammation (Dawson et al., 2003, Expert Opin Ther Targets. 7:35; Daly and Rollins, 2003, Microcir. 10: 247)

The critical role of the CCL2-CCR2 interaction, in modulating the tissue influx of monocytes, has been demonstrated in mice engineered to be deficient in either CCR2 or CCL2. These mice show a selective defect in the migration of macrophages to sites of inflammation (Boring, L., J. et al., 1997, J Clin Invest. 100:2552; Kurihara, T., G. et al., 1997, J Exp Med. 186:1757; Kuziel, W. A., et al 1997, Proc Natl Acad Sci USA. 94:12053; Lu, B., et al., 1998, J Exp Med. 187:601) Maus et al 2005 Am. J. Physiol. Lung Cell. Mol. Physiol. 288: L350-L358; Maus et al 2002; Am. J. Respir. Crit. Care Med. 16: 268). Furthermore, when subjected to disease induction, both CCR2 and CCL2 knockout mice are protected from inflammatory diseases, such as experimental autoimmune encephalomyelitis (EAE; a mouse model for multiple sclerosis) (Huang, D. R., et al., 2001, J Exp Med. 193:713; Izikson, L. R. et al 2000, J Exp Med. 192:1075), neuropathic pain (Abbadie, C., et al., 2003, Proc Natl Acad Sci USA. 100: 7947.), and atherosclerosis (Boring, L., et al., 1998, Nature 394:894).

Chemokines other than CCL2 are agonists for CCR2, and CCL2 may act through receptors other than CCR2. However, in contrast to the redundancy suggested by in vitro studies, in vivo studies using transgenic and knockout models suggest non-redundant roles for CCL2 and CCR2 and a predominantly monocytic chemoattractant role.

CCL2 has been implicated in atherogenesis and in the formation of intimal hyperplasia after arterial injury. It is secreted by endothelial and arterial smooth muscle cells in response to vascular insults, such as hyperlipidemia. This chemokine attracts circulating blood monocytes, which accumulate in early atherosclerotic lesions in the subendothelium, differentiate into macrophages, continue to take up lipids and become foam cells of the fatty streak. CCL2 or CCR2 deficiency, or treatment with antagonists such as 7ND, provided substantial protection against plaque formation (Daly and Rollins, 2003, Microcir. 10: 247; Charo and Taubman, 2004, Circ Res. 95: 858).

CCL2 appears to play a major role in the pathogenesis of Multiple Sclerosis (MS), which involves the infiltration of effector mononuclear cells into the central nervous system. Furthermore, there is a correlation between CCL2 expression and disease activity in MS patients. CCL2 and CCR2 are not necessary for mounting an immune response to myelin antigens, but they are rather required for attracting effector cells into the CNS where they can initiate the process of demyelination and axonal severing that are characteristic of EAE and MS (Daly and Rollins, 2003, Microcir. 10: 247; Mahad and Ransohoff, 2003, Semin. Immunol. 15: 23).

CCR2 and CCL2 contribute to trafficking of macrophages and dendritic cells, an indispensable component of the host response to infectious diseases. Recruitment of T cells to sites of infection is dependent upon a functional CCR2 receptor of the antigen presenting cells (APCs). Several studies with CCR2-deficient mice indicate that the decreased recruitment of such cells leads to a functional Th1-type defect, and to increased susceptibility to various pathogens. CCL2-deficient mice, however, do not have a Th1-type defect, but rather exhibit a Th2-type impairment. These differences can be explained by the redundancy of activation of CCR2 by other MCP cytokines. CCL2 seems to have a direct effect on activated and memory T cells, suggesting its involvement in promoting Th2-type responses. Taken together, these studies support important roles for CCR2 and CCL2 in both the innate and the adaptive immune responses (Charo and Peters, 2003, Microcirc. 10: 259).

Several studies have been published using antagonistic agents to test the potential therapeutic benefits of CCR2 inhibition. The mature human MCP-1, as secreted from cells, has 76 amino acids (Rollins, 1989, Mol. Cell. Biol. 9:4687). Protein antagonists of CCR2, generated by N-terminal truncation of CCL2, namely 7ND (lacking amino acids 2-8 of the mature human MCP-1) and MCP-1(9-76), have been tested in several animal models, and were shown to inhibit experimental restenosis, intimal hyperplasia, pulmonary hypertension, atherosclerosis, focal brain ischemia and ischemia-reperfusion injury, renal fibrosis and injury, nephritis of lupus model mice, renal fibrosis, ischemia-induced neovascularization, hepatic fibrosis, experimental autoimmune myocarditis, and arthritis (Kitamoto and Egashira, 2002, J. Atheroscler. Thromb. 9: 261; Kitamoto and Egashira, 2003, Expert Rev. Cardiovas. Ther. 1: 393).

An antibody generated against murine CCR2 (MC-21) reduces the in vitro activity of MCP-1 by 95%, and almost completely prevented the influx of monocytes in a murine model of acute peritonitis (Mack et al 2001 J. Immunol. 166: 4697). Systemic administration of this antibody was effective also in blocking alveolar monocyte recruitment in response to lung deposition of CCL2 and/or LPS (Maus et al 2005 Am. J. Physiol. Lung Cell. Mol. Physiol. 288: L350-L358; Maus et al 2002, Am. J. Respir. Crit. Care Med. 166: 268). An anti-human CCR2 was effective in a primate model of experimental in-stent restenosis (Horvath et al, 2002, Circ. Res. 90: 488).

There is a growing interest in CCR2 antagonists and hence there are several inhibitors that target the CCR2/CCL2 system which are currently in clinical development including small organic molecules as well as antibodies. For example, INCB3284, Incyte's most advanced CCR2 antagonist, which is currently in Phase IIa clinical trials in rheumatoid arthritis and obese insulin-resistant patients. An additional CCR2 antagonists in Phase II clinical trials are Merck's MK0812, for treatment of relapsing-remitting multiple sclerosis, and Millennium's MLN-1202, a humanized monoclonal antibody specific for CCR2, for the treatment multiple sclerosis, atherosclerosis and scleroderma. Several other agents that target the CCR2/MCP-1 system are in earlier stages of development. For example, CCX915, an orally available CCR2 antagonist is in Phase I development by ChemoCentryx, for treatment of multiple sclerosis. In addition, Telik has an MCP-1 antagonist in preclinical development for treatment of rheumatoid arthritis, multiple sclerosis, inflammatory bowel disease, atherosclerosis, asthma, and cancer.

WO 05/072049 assigned to the applicant of the present invention discloses polynucleotides and their respective encoded polypeptides and assays and methods of use thereof in the diagnosis of endometriosis. One among the hundreds of polynucleotide transcripts disclosed therein is S71513_T2 (denoted herein SEQ ID NO:1) which encodes an amino acid sequence denoted S71513_P2 (denoted herein SEQ ID NO:9), which is disclosed herein to correspond to a splice variant of MCP-1. There is no teaching or suggestion of any utility other than for endometriosis.

Various point mutations of MCP-1 have been studied. Notably, Beall et al. (J. Biol. Chem. 267, 3455-3459, 1992) reported that a double mutation of tyrosine 28 and arginine 30 to leucine and valine, denoted Y28L and R30V respectively, causes a dramatic decrease in chemoattractant activity toward monocytes with the appearance of a novel (IL-8 like) neutrophil chemotactic activity.

U.S. Pat. No. 5,459,128 to Rollins et al. discloses additional point mutations and other variants of MCP-1, including N terminal and C terminal deletions. Mutated MCP-1 derivatives were tested for their ability to inhibit monocyte chemotaxis in vitro in response to non-mutated MCP-1. Only certain point mutations and the N terminal deletion variant denoted 7ND were able to inhibit monocyte chemotaxis. Inhibitory activity was specific for MCP-1 since the mutations did not inhibit monocyte chemotaxis in response to other chemoattractants. Manipulations of the C-terminal α-helix produced proteins that were still able to signal, but had reduced potency compared to wild-type. Deletions of half (D2) or all (D1) of the α-helix yielded proteins with 17% and 11.3% of wild-type activity, respectively. Thus, the findings of this disclosure are teaching away from C terminal deletions having MCP-1 inhibitory effects. U.S. Pat. No. 5,705,360, U.S. Pat. No. 5,739,103 and U.S. Pat. No. 5,854,412 all to Rollins et al. disclose and claim N-terminal deletion mutations of MCP-1 and other chemokines.

Thus, the background art does not teach or suggest inhibitory variants of MCP-1 protein with relatively low homology to human MCP-1 at the C-terminal portion of the molecule. The background art also does not teach or suggest therapeutic utility of MCP-1 variants with deletions or truncations of the predicted C-terminal alpha helix. The background art also does not teach or suggest that such splice variants of MCP-1 protein are useful as therapeutic proteins or peptides for a range of clinical conditions and diseases. The background art also does not teach or suggest that such splice variants of MCP-1 protein are useful as diagnostic markers and/or in diagnostic assays or methods for diagnosis of diseases.

The present invention overcomes deficiencies of the background art by providing MCP-1 therapeutic protein variants and derived peptides, which may be used as active, specific and stable therapeutic proteins or diagnostic markers.

SUMMARY OF THE INVENTION

The present invention provides novel splice variants of MCP-1 and derivatives thereof. Specifically, the present invention provides MCP-1 splice variants and mutants or derivatives thereof having inhibitory effects on MCP-1 activity.

The present invention is of novel MCP-1 variant polypeptides and polynucleotides encoding same, which can be used for the diagnosis, treatment or prevention of a wide range of diseases. The present invention further encompasses pharmaceutical compositions comprising the splice variants, vectors comprising the polynucleotides encoding the splice variants, and host cells comprising such vectors. Unexpectedly, it is now disclosed that various splice variants related by the common feature of C terminal deletions have MCP-1 inhibitory activity.

According to a first aspect the present invention provides novel MCP-1 splice variants having C-terminal deletions or truncations. Unexpectedly, these variants are now disclosed to be efficient inhibitors of native or wild type MCP-1. According to alternative embodiments the present invention further discloses MCP-1 variants having C terminal truncations that may further comprise one or more point mutations. According to alternative embodiments the present invention further discloses derivatives of the novel MCP-1 variants, including but not limited to glycosylation and/or phosphorylation, as well as fusion proteins and/or chemical modifications.

According to certain embodiments, these therapeutic protein variants and derived peptides of the present invention can be modified to form synthetically modified variants according to the present invention, wherein modified variants include but are not limited to fusion proteins (including but not limited to fusion with an Fc fragment of Ig) and/or chemical modifications, including but not limited to pegylation.

Preferably, these therapeutic proteins and derived peptides are useful as therapeutic proteins or peptides for diseases including but not limited to diseases wherein MCP-1 is involved in the etiology or pathogenesis of the disease process, as will be explained in detail hereinbelow.

In particular, diseases amenable to treatment with the splice variants of the invention include:

autoimmune diseases including but not limited to rheumatoid arthritis, multiple sclerosis, scleroderma, systemic lupus erythematosus and inflammatory bowel disease;

vascular disorders, including but not limited to atherosclerosis, restenosis after coronary intervention, intimal hyperplasia, arteriogenesis, ischemia and stroke;

acute and chronic inflammatory lung diseases, including but not limited to idiopathic pulmonary fibrosis, acute respiratory distress syndrome, allergic asthma, bronchiolitis obliterans syndrome and chronic obstructive pulmonary disease;

renal inflammatory diseases and disorders including but not limited to renal fibrosis and injury, nephritis;

disorders involving dysregulation of leptin secretion, such as obesity and cachexia;

allograft survival following various types of organ transplantation;

acute inflammatory conditions, such as sepsis and peritonitis;

other diseases and conditions, both with and without an obvious inflammatory component including endometriosis, atopic dermatitis, pleurisy, allergic inflammation, colitis, polymyositis and dermatomyositis, uveitis, hepatic fibrosis, myocarditis, arthritis, focal brain ischemia and ischemia-reperfusion injury, ischemia-induced neovascularization, neuropathic pain, insulin-resistance type 2 diabetes.

Additionally or alternatively, MCP-1 variants according to the present invention may be useful for diagnosis of diseases wherein MCP-1 is involved in the etiology or pathogenesis of the disease process, as will be explained in detail hereinbelow. It is to be understood that the previously disclosed utility of an MCP-1 variant for diagnosis of endometriosis is specifically excluded. Furthermore, the novel variants may be useful for diagnosis of any disease or condition where MCP-1 is known to serve as a diagnostic or prognostic marker.

"Treatment" also encompasses prevention, amelioration, elimination and control of the disease and/or pathological condition.

According to some particular embodiments the C terminal deletion or truncation extends from amino acid 65 to amino acid 99 of the native or wild type MCP-1. According to a particularly preferred embodiment the MCP-1 variant of the invention is denoted MCP-1-65 and represents a splice variant that is encoded by exons 1, 2 and 3 of the MCP-1 gene with the addition of exon 2a at the exon 2 and 3 junction (SEQ ID NO:1). It should be noted that inclusion of exon 2a at the junction of exons 2 and 3 encodes a polypeptide containing amino acids 1-64 of the wild type or native MCP-1 with one additional unique amino acid namely a methionine residue encoded by exon 2a and the remainder of the polypeptide is terminated. This embodiment is represented herein by SEQ ID NO: 9. Thus, the mature secretory variant MCP-1-65 after removal of the signal peptide will have 42 amino acid residues in total, and is represented herein by SEQ ID NO:35.

Unexpectedly, it was found that truncation or deletion of the predicted alpha helix from the C terminus of the mature MCP-1 molecule, in conjunction with the unique amino acid methionine introduced after the first 41 amino acids of the mature molecule produces an effective and specific inhibitor of the wild type human MCP-1, more effective that the inhibitors known hitherto.

According to other particular embodiments the MCP-1-65 variant of the invention contains at least one point mutation selected from tyrosine 51 to leucine and arginine 53 to valine, denoted Y51L and R53V respectively, corresponding to the two point mutations of MCP-1 reported by Beall et al. (J. Biol. Chem. 267, 3455-3459, 1992), converting tyrosine 28 to leucine and arginine 30 to valine of the mature secretory human MCP-1. MCP-1-65 variants of the invention containing at least one point mutation selected from tyrosine 51 to leucine and arginine 53 to valine, have the amino acid sequences set forth in SEQ ID NOS: 26, 28 and nucleic acid sequences set forth in SEQ ID NO: 27, 29, respectively. According to yet another embodiment the MCP-1-65 variant will contain a double mutation of Y51L and R53R, having the amino acid sequence set forth in SEQ ID NO: 20 and nucleic acid sequence set forth in SEQ ID NOS: 22 or 34. According to other particular embodiments the MCP-1-65 variants of the invention are fused to Fc fragment of IgG, and are represented herein by SEQ ID NO:15 for MCP-1-65-Fc; by SEQ ID NO:21 for an MCP-1-65-Fc containing the double mutation of Y51L and R53V; by SEQ ID NO:30 for an MCP-1-65-Fc containing the Y51L point mutation; and by SEQ ID NO:32 for an MCP-1-65-Fc containing the R53V point mutation. The corresponding optimized nucleic acid sequences encoding the Fc-fused MCP-1 variants of the present invention are represented herein by SEQ ID NO:14 for MCP-1-65-Fc; by SEQ ID NO:23 for an MCP-1-65-Fc containing the double mutation of Y51L and R53V; by SEQ ID NO:31 for an MCP-1-65-Fc containing the Y51L point mutation; and by SEQ ID NO:33 for an MCP-1-65-Fc containing the R53V point mutation.

According to another aspect, the present invention provides an isolated nucleic acid molecule encoding for a splice variant according to the present invention, having a nucleotide sequence as set forth in any one of SEQ ID NOS: 1, 14, 22, 23, 27, 29, 31, 33 or 34 or a sequence complementary thereto.

According to additional aspects, the present invention provides vectors, cells, liposomes and compositions comprising the isolated nucleic acids of this invention.

According to additional aspects, the present invention provides pharmaceutical compositions comprising the novel splice variant polypeptides of this invention.

According to another aspect, the present invention provides an oligonucleotide of at least about 12 nucleotides, specifically hybridizable with the nucleic acid molecules of this invention. In some embodiments, the present invention provides a method for detecting a splice variant nucleic acid sequences in a biological sample, comprising: hybridizing the isolated nucleic acid molecules or oligonucleotide fragments of at least about 12 nucleotides thereof to a nucleic acid material of a biological sample and detecting a hybridization complex; wherein the presence of a hybridization complex correlates with the presence of a splice variant nucleic acid sequence in the biological sample.

These and additional features of the invention will be better understood in conjunction with the figures description, examples and claims which follow.

BRIEF DESCRIPTION OF THE DRAWINGS

FIG. 1a demonstrates amino acid sequence comparison between the MCP1-65 variant of the invention (SEQ ID NO:9) and the known MCP1-WT (SEQ ID NO: 8).

FIG. 1b shows schematic mRNA and protein structure of MCP-1. "WT 99aa" represents the known MCP-1 (SEQ ID NO:8). "65aa" represents the MCP1-65 splice variant of the present invention, SEQ ID NO:9. "Antagonist (deletion 2-8 of mature protein)" represents the known MCP1-92-7ND antagonist (SEQ ID NO:25). Exons are represented by boxes with upper left to lower right fill, while introns are represented by two headed arrows. Proteins are shown in boxes with upper right to lower left fill. The unique regions are represented by white boxes. Homodimerization domain, receptor domain, receptor stabilization domain and GAB binding sites are identified accordingly.

FIG. 2 shows the optimized nucleotide sequences of MCP-1 variants prepared for cloning in the expression vector pIRESpuro3, and their respective protein sequences. DNA sequences in bold show the relevant ORFs (open reading frames). FIG. 2A shows MCP1-99 nucleotide and protein sequences, SEQ ID NOS: 10 and 11, respectively. The Strep-His tag is underlined. FIG. 2B shows MCP1 92 7ND nucleotide and protein sequences, SEQ ID NOS: 12 and 13, respectively. The Strep-His tag is underlined. FIG. 2C shows MCP1-65 Fc nucleotide and protein sequences, SEQ ID NOS: 14 and 15, respectively. The Fc sequence is underlined. N297A mutation creating the non-glycosilated Fc mutant is shown in Italic.

FIG. 3 shows a schematic map of polynucleotide coding for MCP-1-65-Fc Mut in the pIRESpuro3 expression vector.

FIG. 4 shows Western blot analysis, demonstrating stable MCP-1 expression.

FIG. 5 shows Coomassie staining results of SDS-PAGE gel of MCP-1 variants. FIG. 5A demonstrates the SDS-PAGE results of the MCP-1-99; FIG. 5B demonstrates SDS-PAGE results of MCP-1-92-7ND; FIG. 5C demonstrates SDS-PAGE results of MCP-1-65m-Fc.

DESCRIPTION OF PREFERRED EMBODIMENTS

Figure 4A:
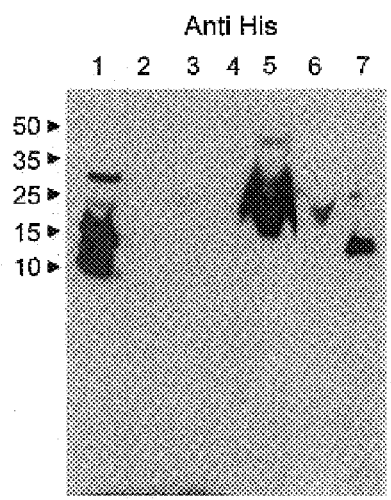
FIG. 4A demonstrates the MCP-1-99 (SEQ ID NO: 11) expression, using anti His antibodies. Lane 1 represents Molecular weight marker (Rainbow AMERSHAM RPN800); lane 2 represents mock pIRESpuro3; lane 5 represents MCP-1-99 (SEQ ID NO: 11); lane 7 represents His control (~100 ng).

The present invention provides MCP-1 protein variants, which may optionally be used for therapeutic applications and/or as diagnostic markers.

Preferably, but without wishing to be limited, these therapeutic protein variants are inhibitory peptides antagonistic to the activity of MCP-1 and as such are useful as therapeutic proteins or peptides for diseases in which MCP-1 is involved either in the etiology or pathogenesis of the disease or disorder.

Diseases treatable by the variants are described herein and are collectively referred to as "variant-treatable diseases". A "variant-treatable" disease refers to any disease that is treatable by using a splice variant of MCP-1 having a C terminal deletion or truncation or their derived peptides according to the present invention. Preferably, a "variant-treatable" disease is selected from the group including but not limited to:

autoimmune diseases including but not limited to rheumatoid arthritis, multiple sclerosis, scleroderma, systemic lupus erythematosus and inflammatory bowel disease;

vascular disorders, including but not limited to atherosclerosis, restenosis after coronary intervention, intimal hyperplasia, arteriogenesis, ischemia and stroke;

acute and chronic inflammatory lung diseases, including but not limited to idiopathic pulmonary fibrosis, acute respiratory distress syndrome, allergic asthma, bronchiolitis obliterans syndrome and chronic obstructive pulmonary disease;

renal inflammatory diseases and disorders including but not limited to renal fibrosis and injury, nephritis; disorders involving deregulation of leptin secretion, such as obesity and cachexia;

allograft survival following various types of organ transplantation; acute inflammatory conditions, such as sepsis and peritonitis;

other diseases and conditions, both with and without an obvious inflammatory component including endometriosis, atopic dermatitis, pleurisy, allergic inflammation, colitis, polymyositis and dermatomyositis, uveitis, hepatic fibrosis, myocarditis, arthritis, focal brain ischemia and ischemia-reperfusion injury, ischemia-induced neovascularization, neuropathic pain, insulin-resistance type 2 diabetes.

Furthermore, the novel variants may be useful for diagnosis of any disease or condition where MCP-1 is known to serve as a diagnostic or prognostic marker. Additionally, or alternatively, MCP-1 variants according to the present invention may be useful for diagnosis of autoimmune diseases including but not limited to rheumatoid arthritis, multiple sclerosis, scleroderma, systemic lupus erythematosus and inflammatory bowel disease; vascular disorders, including but not limited to atherosclerosis, restenosis after coronary intervention, intimal hyperplasia, arteriogenesis, ischemia and stroke; acute and chronic inflammatory lung diseases, including but not limited to idiopathic pulmonary fibrosis, acute respiratory distress syndrome, allergic asthma, bronchiolitis obliterans syndrome and chronic obstructive pulmonary disease; renal inflammatory diseases and disorders including but not limited to renal fibrosis and injury, nephritis; disorders involving deregulation of leptin secretion, such as obesity and cachexia; allograft survival following various types of organ transplantation; acute inflammatory conditions, such as sepsis and peritonitis; other diseases and conditions, both with and without an obvious inflammatory component including endometriosis, atopic dermatitis, pleurisy, allergic inflammation, colitis, polymyositis and dermatomyositis, uveitis, hepatic fibrosis, myocarditis, arthritis, focal brain ischemia and ischemia-reperfusion injury, ischemia-induced neovascularization, neuropathic pain, insulin-resistance type 2 diabetes. It is to be understood that the previously disclosed utility of an MCP-1 variant (SEQ ID NO:9) for diagnosis or treatment of endometriosis (WO 2005/072049) is specifically excluded.

Description of the Methodology Undertaken to Uncover the Biomolecular Sequences of the Present Invention Human ESTs and cDNAs were obtained from GenBank versions 145 (Dec. 23, 2004 ftp://ftp.ncbi.nih.gov/genbank/release.notes/gb145136.release.notes) and NCBI genome assembly of Aug. 26, 2005 (Build 35). Novel splice variants were predicted using the LEADS clustering and assembly system as described in U.S. Pat. No. 6,625,545, U.S. patent application Ser. No. 10/426,002, both of which are hereby incorporated by reference as if fully set forth herein. Briefly, the software cleans the expressed sequences from repeats, vectors and immunoglobulins. It then aligns the expressed sequences to the genome taking alternative splicing into account and clusters overlapping expressed sequences into "clusters" that represent genes or partial genes.

These were annotated using the GeneCarta (Compugen, Tel-Aviv, Israel) platform. The GeneCarta platform includes a rich pool of annotations, sequence information (particularly of spliced sequences), chromosomal information, alignments, and additional information such as SNPs, gene ontology terms, expression profiles, functional analyses, detailed domain structures, known and predicted proteins and detailed homology reports.

Brief description of the methodology used to obtain annotative sequence information is summarized infra (for detailed description see U.S. patent application Ser. No. 10/426,002, published as US20040101876).

The ontological annotation approach—An ontology refers to the body of knowledge in a specific knowledge domain or discipline such as molecular biology, microbiology, immunology, virology, plant sciences, pharmaceutical chemistry, medicine, neurology, endocrinology, genetics, ecology, genomics, proteomics, cheminformatics, pharmacogenomics, bioinformatics, computer sciences, statistics, mathematics, chemistry, physics and artificial intelligence.

An ontology includes domain-specific concepts—referred to, herein, as sub-ontologies. A sub-ontology may be classified into smaller and narrower categories. The ontological annotation approach is effected as follows.

First, biomolecular (i.e., polynucleotide or polypeptide) sequences are computationally clustered according to a progressive homology range, thereby generating a plurality of clusters each being of a predetermined homology of the homology range.

Progressive homology is used to identify meaningful homologies among biomolecular sequences and to thereby assign new ontological annotations to sequences, which share requisite levels of homologies. Essentially, a biomolecular sequence is assigned to a specific cluster if displays a predetermined homology to at least one member of the cluster (i.e., single linkage). A "progressive homology range" refers to a range of homology thresholds, which progress via predetermined increments from a low homology level (e.g. 35%) to a high homology level (e.g. 99%).

Following generation of clusters, one or more ontologies are assigned to each cluster. Ontologies are derived from an annotation preassociated with at least one biomolecular sequence of each cluster; and/or generated by analyzing (e.g., text-mining) at least one biomolecular sequence of each cluster thereby annotating biomolecular sequences.

The hierarchical annotation approach—"Hierarchical annotation" refers to any ontology and subontology, which can be hierarchically ordered, such as, a tissue expression hierarchy, a developmental expression hierarchy, a pathological expression hierarchy, a cellular expression hierarchy, an intracellular expression hierarchy, a taxonomical hierarchy, a functional hierarchy and so forth.

The hierarchical annotation approach is effected as follows. First, a dendrogram representing the hierarchy of interest is computationally constructed. A "dendrogram" refers to a branching diagram containing multiple nodes and representing a hierarchy of categories based on degree of similarity or number of shared characteristics.

Each of the multiple nodes of the dendrogram is annotated by at least one keyword describing the node, and enabling literature and database text mining, such as by using publicly available text mining software. A list of keywords can be obtained from the GO Consortium (www.geneontlogy.org). However, measures are taken to include as many keywords, and to include keywords which might be out of date. For example, for tissue annotation, a hierarchy is built using all available tissue/libraries sources available in the GenBank, while considering the following parameters: ignoring GenBank synonyms, building anatomical hierarchies, enabling flexible distinction between tissue types (normal versus pathology) and tissue classification levels (organs, systems, cell types, etc.).

In a second step, each of the biomolecular sequences is assigned to at least one specific node of the dendrogram.

The biomolecular sequences can be annotated biomolecular sequences, unannotated biomolecular' sequences or partially annotated biomolecular sequences.

Annotated biomolecular sequences can be retrieved from pre-existing annotated databases as described hereinabove.

For example, in GenBank, relevant annotational information is provided in the definition and keyword fields. In this case, classification of the annotated biomolecular sequences to the dendrogram nodes is directly effected. A search for suitable annotated biomolecular sequences is performed using a set of keywords which are designed to classify the biomolecular sequences to the hierarchy (i.e., same keywords that populate the dendrogram).

In cases where the biomolecular sequences are unannotated or partially annotated, extraction of additional annotational information is effected prior to classification to dendrogram nodes. This can be effected by sequence alignment, as described hereinabove. Alternatively, annotational information can be predicted from structural studies. Where needed, nucleic acid sequences can be transformed to amino acid sequences to thereby enable more accurate annotational prediction.

Finally, each of the assigned biomolecular sequences is recursively classified to nodes hierarchically higher than the specific nodes, such that the root node of the dendrogram encompasses the full biomolecular sequence set, which can be classified according to a certain hierarchy, while the offspring of any node represent a partitioning of the parent set.

For example, a biomolecular sequence found to be specifically expressed in "rhabdomyosarcoma", will be classified also to a higher hierarchy level, which is "sarcoma", and then to "Mesenchymal cell tumors" and finally to a highest hierarchy level "Tumor". In another example, a sequence found to be differentially expressed in endometrium cells, will be classified also to a higher hierarchy level, which is "uterus", and then to "women genital system" and to "genital system" and finally to a highest hierarchy level "genitourinary system". The retrieval can be performed according to each one of the requested levels.

Annotating gene expression according to relative abundance—Spatial and temporal gene annotations are also assigned by comparing relative abundance in libraries of different origins. This approach can be used to find genes, which are differentially expressed in tissues, pathologies and different developmental stages. In principal, the presentation of a contigue in at least two tissues of interest is determined and significant over or under representation of the contigue in one of the at least two tissues is assessed to identify differential expression. Significant over or under representation is analyzed by statistical pairing.

Annotating spatial and temporal expression can also be effected on splice variants. This is effected as follows. First, a contigue which includes exonal sequence presentation of the at least two splice variants of the gene of interest is obtained. This contigue is assembled from a plurality of expressed sequences. Then, at least one contigue sequence region, unique to a portion (i.e., at least one and not all) of the at least two splice variants of the gene of interest, is identified. Identification of such unique sequence region is effected using computer alignment software. Finally, the number of the plurality of expressed sequences in the tissue having the at least one contigue sequence region is compared with the number of the plurality of expressed sequences not-having the at least one contigue sequence region, to thereby compare the expression level of the at least two splice variants of the gene of interest in the tissue.

Data concerning therapies, indications and possible pharmacological activities of the polypeptides of the present invention was obtained from PharmaProject (PJB Publications Ltd 2003 http://www.pjbpubs.com/cms.asp-?pageid=340) and public databases, including LocusLink (http://www.genelynx.org/cgi-bin/resource?res=locuslink) and Swissprot (http://www.ebi.ac.uk/swissprot/index.html). Functional structural analysis of the polypeptides of the present invention was effected using Interpro domain analysis software (Interpro default parameters, the analyses that were run are HMMPfam, HMMSmart, ProfileScan, Fprint-Scan, and BlastProdom). Subcellular localization was analyzed using ProLoc software (Einat Hazkani-Covo, Erez Y. Levanon, Galit Rotman, Dan Graur, Amit Novik. Evolution of multicellularity in metazoa: comparative analysis of the subcellular localization of proteins in *Saccharomyces, Drosophila* and *Caenorhabditis*. Cell Biology International (2004; 28(3):171-8).

Prediction of Cellular Localization

Information given in the text with regard to cellular localization was determined according to four different software programs: (i) tmhmm (from Center for Biological Sequence Analysis, Technical University of Denmark DTU, http://www.cbs.dtu.dk/services/TMHMM/TMHMM2.0b.guide. php) or (ii) tmpred (from EMBnet, maintained by the ISREC Bioinformatics group and the LICR Information Technology Office, Ludwig Institute for Cancer Research, Swiss Institute of Bioinformatics, http://www.ch.embnet.org/software/TM-PRED_form.html) for transmembrane region prediction; (iii) signalp_hmm and (iv) signalp_nn (both from Center for Biological Sequence Analysis, Technical University of Denmark DTU, http://www.cbs.dtu.dk/services/SignalP/background/prediction.php) for signal peptide prediction. The terms "sig-nalp_hmm" and "signalp_nn" refer to two modes of operation for the program SignalP: hmm refers to Hidden Markov Model, while nn refers to neural networks. Localization was also determined through manual inspection of known protein localization and/or gene structure, and the use of heuristics by the individual inventor. In some cases for the manual inspection of cellular localization prediction, inventors used the ProLoc computational platform [Einat Hazkani-Covo, Erez Levanon, Galit Rotman, Dan Graur and Amit Novik; (2004) Evolution of multicellularity in metazoa: comparative analysis of the subcellular localization of proteins in *Saccharomyces, Drosophila* and *Caenorhabditis*. Cell Biology International 2004; 28(3):171-8.], which predicts protein localization based on various parameters including, protein domains (e.g., prediction of trans-membranous regions and localization thereof within the protein), pI, protein length, amino acid composition, homology to pre-annotated proteins, recognition of sequence patterns which direct the protein to a certain organelle (such as, nuclear localization signal, NLS, mitochondria localization signal), signal peptide and anchor modeling and using unique domains from Pfam that are specific to a single compartment.

Single Nucleotide Polymorphisms

Information is given in the text with regard to SNPs (single nucleotide polymorphisms). A description of the abbreviations is as follows. "T→C", for example, means that the SNP results in a change at the position given in the table from T to C. Similarly, "M→Q", for example, means that the SNP has caused a change in the corresponding amino acid sequence, from methionine (M) to glutamine (Q). If, in place of a letter at the right hand side for the nucleotide sequence SNP, there is a space, it indicates that a frameshift has occurred. A frameshift may also be indicated with a hyphen (-). A stop codon is indicated with an asterisk at the right hand side (*). As part of the description of an SNP, a comment may be found in parentheses after the above description of the SNP itself. This comment may include an FTId, which is an identifier to a SwissProt entry that was created with the indicated SNP. An FTId is a unique and stable feature identifier, which allows construction of links directly from position-specific annotation in the feature table to specialized protein-related databases. The FTId is always the last component of a feature in the description field, as follows: FTId=XXX_number, in which XXX is the 3-letter code for the specific feature key, separated by an underscore from a 6-digit number. In the table of the amino acid mutations of the wild type proteins of the selected splice variants of the invention, the header of the first column is "SNP position(s) on amino acid sequence", representing a position of a known mutation on amino acid sequence. For each given SNP, it was determined whether it was previously known by using dbSNP build 122 from NCBI, released on Aug. 13, 2004.

Information given in the text with regard to the Homology to the wild type was determined by Smith-Waterman version 5.1.2

Using Special (Non Default) Parameters as Follows:
   model=sw.model
   GAPEXT=0
   GAPOP=100.0
   MATRIX=blosum 100

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). All of these are hereby incorporated by reference as if fully set forth herein. As used herein, the following terms have the meanings ascribed to them unless specified otherwise.

Assays, Terms and Definitions

As used herein the phrase "disease" includes any type of pathology and/or damage, including both chronic and acute damage, as well as a progress from acute to chronic damage.

The term "biologically active", as used herein, refers to a protein having structural, regulatory, or biochemical functions of a naturally occurring molecule. Likewise, "immunologically active" refers to the capability of the natural, recombinant, or synthetic ligand, or any oligopeptide thereof, to induce a specific immune response in appropriate animals or cells and to bind with specific antibodies.

The term "modulate", as used herein, refers to a change in the activity of at least one receptor-mediated activity. For example, modulation may cause an increase or a decrease in protein activity, binding characteristics, or any other biological, functional or immunological properties of a ligand.

Nucleic Acids

A "nucleic acid fragment" or an "oligonucleotide" or a "polynucleotide" are used herein interchangeably to refer to a polymer of nucleic acid residues. A polynucleotide sequence of the present invention refers to a single or double stranded nucleic acid sequences which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is composed of genomic and cDNA sequences. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

Thus, the present invention encompasses nucleic acid sequences described hereinabove; fragments thereof, sequences hybridizable therewith, sequences homologous thereto [e.g., at least 90%, at least 95% or more identical to the nucleic acid sequences set forth herein], sequences encoding similar polypeptides with different codon usage, altered sequences characterized by mutations, such as deletion, insertion or substitution of one or more nucleotides, either naturally occurring or man induced, either randomly or in a targeted fashion. The present invention also encompasses homologous nucleic acid sequences (i.e., which form a part of a polynucleotide sequence of the present invention), which include sequence regions unique to the polynucleotides of the present invention.

In cases where the polynucleotide sequences of the present invention encode previously unidentified polypeptides, the present invention also encompasses novel polypeptides or portions thereof, which are encoded by the isolated polynucleotide and respective nucleic acid fragments thereof described hereinabove.

Thus, the present invention also encompasses polypeptides encoded by the polynucleotide sequences of the present invention. The present invention also encompasses homologues of these polypeptides, such homologues can be at least 90%, at least 95% or more homologous to the amino acid sequences set forth below, as can be determined using BlastP software of the National Center of Biotechnology Information (NCBI) using default parameters. Finally, the present invention also encompasses fragments of the above described polypeptides and polypeptides having mutations, such as deletions, insertions or substitutions of one or more amino acids, either naturally occurring or man induced, either randomly or in a targeted fashion.

As mentioned hereinabove, biomolecular sequences uncovered using the methodology of the present invention can be efficiently utilized as tissue or pathological markers and as putative drugs or drug targets for treating or preventing a disease.

Oligonucleotides designed for carrying out the methods of the present invention for any of the sequences provided herein (designed as described above) can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art.

Oligonucleotides used according to this aspect of the present invention are those having a length selected from a range of about 10 to about 200 bases preferably about 15 to about 150 bases, more preferably about 20 to about 100 bases, most preferably about 20 to about 50 bases.

The oligonucleotides of the present invention may comprise heterocyclic nucleosides consisting of purines and the pyrimidines bases, bonded in a 3' to 5' phosphodiester linkage.

Preferable oligonucleotides are those modified in either backbone, internucleoside linkages or bases, as is broadly described hereinunder. Such modifications can oftentimes facilitate oligonucleotide uptake and resistivity to intracellular conditions.

Specific examples of preferred oligonucleotides useful according to this aspect of the present invention include oligonucleotides containing modified backbones or non-natural internucleoside linkages. Oligonucleotides having modified backbones include those that retain a phosphorus atom in the backbone, as disclosed in U.S. Pat. Nos. 4,469,863; 4,476, 301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide backbones include, for example, phosphorothioates, chiral phosphorothioates, phosphorodithioates, phosphotriesters, aminoalkyl phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms can also be used.

Alternatively, modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other oligonucleotides which can be used according to the present invention, are those modified in both sugar and the internucleoside linkage, i.e., the backbone, of the nucleotide units are replaced with novel groups. The base units are maintained for complementation with the appropriate polynucleotide target. An example for such an oligonucleotide mimetic, includes peptide nucleic acid (PNA). A PNA oligonucleotide refers to an oligonucleotide where the sugar-backbone is replaced with an amide containing backbone, in particular an aminoethylglycine backbone. The bases are retained and are bound directly or indirectly to aza nitrogen atoms of the amide portion of the backbone. U.S. patents that teach the preparation of PNA compounds include, but are not limited to, U.S. Pat. Nos. 5,539,082; 5,714,331; and 5,719, 262, each of which is herein incorporated by reference. Other backbone modifications, which can be used in the present invention are disclosed in U.S. Pat. No. 6,303,374.

Oligonucleotides of the present invention may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia Of Polymer Science and Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B. , ed., CRC Press, 1993. Such bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi Y S et al. (1993) Antisense Research and Applications, CRC Press, Boca Raton 276-278] and are presently preferred base substitutions, even more particularly when combined with 2'-O-methoxyethyl sugar modifications.

Another modification of the oligonucleotides of the invention involves chemically linking to the oligonucleotide one or more moieties or conjugates, which enhance the activity, cellular distribution or cellular uptake of the oligonucleotide. Such moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety, as disclosed in U.S. Pat. No. 6,303,374.

It is not necessary for all positions in a given oligonucleotide molecule to be uniformly modified, and in fact more than one of the aforementioned modifications may be incorporated in a single compound or even at a single nucleoside within an oligonucleotide.

Antibodies

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'$_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, CH1, CH2 and CH3, but does not include the heavy chain variable region.

The functional fragments of antibodies, such as Fab, F(ab') 2, and Fv that are capable of binding to macrophages, are described as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab') or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321: 522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10,: 779-783 (1992); Lonberg et al., Nature 368: 856-859 (1994); Morrison, Nature 368 812-13 (1994);

Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Monoclonal antibody development may optionally be performed according to any method that is known in the art. The methods described in WO 2005/072049 are expressly incorporated by reference as if fully set forth herein.

Oligonucleotides

Oligonucleotides according to the present invention may optionally be used as molecular probes as described herein. Such probes are useful for hybridization assays, and also for NAT assays (as primers, for example).

Thus, the present invention encompasses nucleic acid sequences described hereinabove; fragments thereof, sequences hybridizable therewith, sequences homologous thereto, sequences encoding similar polypeptides with different codon usage, altered sequences characterized by mutations, such as deletion, insertion or substitution of one or more nucleotides, either naturally occurring or man induced, either randomly or in a targeted fashion.

Typically, detection of a nucleic acid of interest in a biological sample is effected by hybridization-based assays using an oligonucleotide probe.

The term "oligonucleotide" refers to a single stranded or double stranded oligomer or polymer of ribonucleic acid (RNA) or deoxyribonucleic acid (DNA) or mimetics thereof. This term includes oligonucleotides composed of naturally-occurring bases, sugars and covalent internucleoside linkages (e.g., backbone) as well as oligonucleotides having non-naturally-occurring portions which function similarly to respective naturally-occurring portions. An example of an oligonucleotide probe which can be utilized by the present invention is a single stranded polynucleotide which includes a sequence complementary to the unique sequence region of any variant according to the present invention, including but not limited to a nucleotide sequence coding for an amino sequence of a bridge, tail, head and/or insertion according to the present invention, and/or the equivalent portions of any nucleotide sequence given herein (including but not limited to a nucleotide sequence of a node, segment or amplicon described herein).

Alternatively, an oligonucleotide probe of the present invention can be designed to hybridize with a nucleic acid sequence encompassed by any of the above nucleic acid sequences, particularly the portions specified above, including but not limited to a nucleotide sequence coding for an amino sequence of a bridge, tail, head and/or insertion according to the present invention, and/or the equivalent portions of any nucleotide sequence given herein (including but not limited to a nucleotide sequence of a node, segment or amplicon described herein).

Oligonucleotides designed according to the teachings of the present invention can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988) and "Oligonucleotide Synthesis" Gait, M. J., ed. (1984) utilizing solid phase chemistry, e.g. cyanoethyl phosphoramidite followed by deprotection, desalting and purification by for example, an automated trityl-on method or HPLC.

Oligonucleotides of the present invention may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Such bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi Y S et al. (1993) Antisense Research and Applications, CRC Press, Boca Raton 276-278] and are presently preferred base substitutions, even more particularly when combined with 2'-O-methoxyethyl sugar modifications.

It will be appreciated that oligonucleotides of the present invention may include further modifications which increase bioavailability, therapeutic efficacy and reduce cytotoxicity. Such modifications are described in Younes (2002) Current Pharmaceutical Design 8:1451-1466.

The isolated polynucleotides of the present invention can optionally be detected (and optionally quantified) by using hybridization assays. Thus, the isolated polynucleotides of the present invention are preferably hybridizable with any of the above described nucleic acid sequences under moderate to stringent hybridization conditions.

Moderate to stringent hybridization conditions are characterized by a hybridization solution such as containing 10% dextran sulfate, 1 M NaCl, 1% SDS and 5×10$^6$ cpm $^{32}$P labeled probe, at 65° C., with a final wash solution of 0.2× SSC and 0.1% SDS and final wash at 65° C. and whereas moderate hybridization is effected using a hybridization solution containing 10% dextran sulfate, 1 M NaCl, 1% SDS and 5×10$^6$ cpm $^{32}$p labeled probe, at 65° C., with a final wash solution of 1×SSC and 0.1% SDS and final wash at 50° C.

Hybridization based assays which allow the detection of the biomarkers of the present invention (i.e., DNA or RNA) in a biological sample rely on the use of oligonucleotides which can be 10, 15, 20, or 30 to 100 nucleotides long, preferably from 10 to 50, and more preferably from 40 to 50 nucleotides.

Hybridization of short nucleic acids (below 200 bp in length, e.g. 17-40 bp in length) can be effected using the following exemplary hybridization protocols which can be modified according to the desired stringency; (i) hybridization solution of 6×SSC and 1% SDS or 3 M TMACI, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 1-1.5° C. below the $T_m$, final wash solution of 3 M TMACI, 0.01 M sodium phosphate (pH 6.8), 1 mM EDTA (pH 7.6), 0.5% SDS at 1-1.5° C. below the $T_m$; (ii) hybridization solution of 6×SSC and 0.1% SDS or 3 M TMACI, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 2-2.5° C. below the $T_m$, final wash solution of 3 M TMACI, 0.01 M sodium phosphate (pH 6.8), 1 mM EDTA (pH 7.6), 0.5% SDS at 1-1.5° C. below the Tm, final wash solution of 6×SSC, and final wash at 22° C.; (iii) hybridization solution of 6×SSC and 1% SDS or 3 M TMACI, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature.

The detection of hybrid duplexes can be carried out by a number of methods. Typically, hybridization duplexes are separated from unhybridized nucleic acids and the labels bound to the duplexes are then detected. Such labels refer to radioactive, fluorescent, biological or enzymatic tags or labels of standard use in the art. A label can be conjugated to either the oligonucleotide probes or the nucleic acids derived from the biological sample (target).

For example, oligonucleotides of the present invention can be labeled subsequent to synthesis, by incorporating biotinylated dNTPs or rNTP, or some similar means (e.g., photocross-linking a psoralen derivative of biotin to RNAS), followed by addition of labeled streptavidin (e.g., phycoerythrin-conjugated streptavidin) or the equivalent. Alternatively, when fluorescently-labeled oligonucleotide probes are used, fluorescein, lissamine, phycoerythrin, rhodamine (Perkin Elmer Cetus), Cy2, Cy3, Cy3.5, Cy5, Cy5.5, Cy7, FluorX (Amersham) and others [e.g., Kricka et al. (1992), Academic Press San Diego, Calif.] can be attached to the oligonucleotides.

Traditional hybridization assays include PCR, RT-PCR, Real-time PCR, RNase protection, in-situ hybridization, primer extension, Southern blots (DNA detection), dot or slot blots (DNA, RNA), and Northern blots (RNA detection) (NAT type assays are described in greater detail below). More recently, PNAs have been described (Nielsen et al. 1999, Current Opin. Biotechnol. 10:71-75). Other detection methods include kits containing probes on a dipstick setup and the like.

Although the present invention is not specifically dependent on the use of a label for the detection of a particular nucleic acid sequence, such a label might be beneficial, by increasing the sensitivity of the detection.

Furthermore, it enables automation. Probes can be labeled according to numerous well known methods (Sambrook et al., 1989, supra). Non-limiting examples of radioactive labels include 3H, 14C, 32P, and 35S. Non-limiting examples of detectable markers include ligands, fluorophores, chemiluminescent agents, enzymes, and antibodies. Other detectable markers for use with probes, which can enable an increase in sensitivity of the method of the invention, include biotin and radio-nucleotides. It will become evident to the person of ordinary skill that the choice of a particular label dictates the manner in which it is bound to the probe.

As commonly known, radioactive nucleotides can be incorporated into probes of the invention by several methods. Non-limiting examples thereof include kinasing the 5' ends of the probes using gamma ATP and polynucleotide kinase, using the Klenow fragment of Pol I of E coli in the presence of radioactive dNTP (i.e. uniformly labeled DNA probe using random oligonucleotide primers in low-melt gels), using the SP6/T7 system to transcribe a DNA segment in the presence of one or more radioactive NTP, and the like.

Those skilled in the art will appreciate that wash steps may be employed to wash away excess target DNA or probe as well as unbound conjugate. Further, standard heterogeneous assay formats are suitable for detecting the hybrids using the labels present on the oligonucleotide primers and probes.

It will be appreciated that a variety of controls may be usefully employed to improve accuracy of hybridization assays. For instance, samples may be hybridized to an irrelevant probe and treated with RNAse A prior to hybridization, to assess false hybridization.

Probes of the invention can be utilized with naturally occurring sugar-phosphate backbones as well as modified backbones including phosphorothioates, dithionates, alkyl phosphonates and a-nucleotides and the like. Modified sugar-phosphate backbones are generally taught by Miller, 1988, Ann. Reports Med. Chem. 23:295 and Moran et al., 1987, Nucleic acid molecule. Acids Res., 14:5019. Probes of the invention can be constructed of either ribonucleic acid (RNA) or deoxyribonucleic acid (DNA), and preferably of DNA.

Detection (and optionally quantification) of a nucleic acid of interest in a biological sample may also optionally be effected by NAT-based assays, which involve nucleic acid amplification technology, such as PCR for example (or variations thereof such as real-time PCR for example).

Amplification of a selected, or target, nucleic acid sequence may be carried out by a number of suitable methods. See generally Kwoh et al., 1990, Am. Biotechnol. Lab. 8:14 Numerous amplification techniques have been described and can be readily adapted to suit particular needs of a person of ordinary skill. Non-limiting examples of amplification techniques include polymerase chain reaction (PCR), ligase chain reaction (LCR), strand displacement amplification (SDA), transcription-based amplification, the q3 replicase system and NASBA (Kwoh et al., 1989, Proc. Natl. Acad. Sci. USA 86, 1173-1177; Lizardi et al., 1988, BioTechnology 6:1197-1202; Malek et al., 1994, Methods Mol. Biol., 28:253-260; and Sambrook et al., 1989, supra).

Polymerase chain reaction (PCR) is carried out in accordance with known techniques, as described for example, in U.S. Pat. Nos. 4,683,195; 47683,202; 4,800,159; and 4,965,188 (the disclosures of all three U.S. patents are incorporated herein by reference). In general, PCR involves a treatment of a nucleic acid sample (e.g., in the presence of a heat stable DNA polymerase) under hybridizing conditions, with one oligonucleotide primer for each strand of the specific sequence to be detected. An extension product of each primer, which is synthesized is complementary to each of the two nucleic acid strands, with the primers sufficiently complementary to each strand of the specific sequence to hybridize therewith. The extension product synthesized from each primer can also serve as a template for further synthesis of extension products using the same primers. Following a sufficient number of rounds of synthesis of extension products, the sample is analyzed to assess whether the sequence or sequences to be detected are present. Detection of the amplified sequence may be carried out by visualization following EtBr staining of the DNA following gel electrophoresis, or using a detectable label in accordance with known techniques, and the like. For a review of PCR techniques, see PCR Protocols, A Guide to Methods and Amplifications, Michael et al. Eds, Acad. Press, 1990.

As used herein, a "primer" defines an oligonucleotide which is capable of annealing to a target sequence, thereby creating a double stranded region which can serve as an initiation point for DNA synthesis under suitable conditions.

Ligase chain reaction (LCR) is carried out in accordance with known techniques (Weiss, 1991, Science 254:1292). Adaptation of the protocol to meet the desired needs can be carried out by a person of ordinary skill. Strand displacement amplification (SDA) is also carried out in accordance with known techniques or adaptations thereof to meet the particular needs (Walker et al., 1992, Proc. Natl. Acad. Sci. USA 89:392-396; and ibid., 1992, Nucleic Acids Res. 20:1691-1696).

The terminology "amplification pair" refers herein to a pair of oligonucleotides (oligos) of the present invention, which are selected to be used together in amplifying a selected nucleic acid sequence by one of a number of types of amplification processes, preferably a polymerase chain reaction. Other types of amplification processes include ligase chain reaction, strand displacement amplification, or nucleic acid sequence-based amplification, as explained in greater detail below. As commonly known in the art, the oligos are designed to bind to a complementary sequence under selected conditions.

In one particular embodiment, amplification of a nucleic acid sample from a patient is amplified under conditions which favor the amplification of the most abundant differentially expressed nucleic acid. In one preferred embodiment, RT-PCR is carried out on an mRNA sample from a patient under conditions which favor the amplification of the most abundant mRNA. In another preferred embodiment, the amplification of the differentially expressed nucleic acids is carried out simultaneously. Of course, it will be realized by a person skilled in the art that such methods could be adapted for the detection of differentially expressed proteins instead of differentially expressed nucleic acid sequences.

The nucleic acid (i.e. DNA or RNA) for practicing the present invention may be obtained according to well known methods.

Oligonucleotide primers of the present invention may be of any suitable length, depending on the particular assay format and the particular needs and targeted genomes employed. In general, the oligonucleotide primers are at least 12 nucleotides in length, preferably between 15 and 24 molecules, and they may be adapted to be especially suited to a chosen nucleic acid amplification system. As commonly known in the art, the oligonucleotide primers can be designed by taking into consideration the melting point of hybridization thereof with its targeted sequence (see below and in Sambrook et al., 1989, Molecular Cloning—A Laboratory Manual, 2nd Edition, CSH Laboratories; Ausubel et al., 1989, in Current Protocols in Molecular Biology, John Wiley & Sons Inc., N.Y.).

It will be appreciated that antisense oligonucleotides may be employed to quantify expression of a splice isoform of interest. Such detection is effected at the pre-mRNA level. Essentially the ability to quantitate transcription from a splice site of interest can be effected based on splice site accessibility. Oligonucleotides may compete with splicing factors for the splice site sequences. Thus, low activity of the antisense oligonucleotide is indicative of splicing activity [see Sazani and Kole (2003), supra].

Polymerase chain reaction (PCR)-based methods may be used to identify the presence of mRNA of the markers of the present invention. For PCR-based methods a pair of oligonucleotides is used, which is specifically hybridizable with the polynucleotide sequences described hereinabove in an opposite orientation so as to direct exponential amplification of a portion thereof (including the hereinabove described sequence alteration) in a nucleic acid amplification reaction. For example, oligonucleotide pairs of primers specifically hybridizable with nucleic acid sequences according to the present invention are described in greater detail with regard to the Examples below.

The polymerase chain reaction and other nucleic acid amplification reactions are well known in the art (various non-limiting examples of these reactions are described in greater detail below). The pair of oligonucleotides according to this aspect of the present invention are preferably selected to have compatible melting temperatures (Tm), e.g., melting temperatures which differ by less than that 7° C., preferably less than 5° C., more preferably less than 4° C., most preferably less than 3° C., ideally between 3° C. and 0° C.

Hybridization to oligonucleotide arrays may be also used to determine expression of the biomarkers of the present invention (hybridization itself is described above). Such screening has been undertaken in the BRCA1 gene and in the protease gene of HIV-1 virus [see Hacia et al., (1996) Nat Genet 1996; 14(4):441-447; Shoemaker et al., (1996) Nat Genet 1996; 14(4):450-456; Kozal et al., (1996) Nat Med 1996; 2(7):753-759]. Optionally and preferably, such hybridization is combined with amplification as described herein.

The nucleic acid sample which includes the candidate region to be analyzed is preferably isolated, amplified and labeled with a reporter group. This reporter group can be a fluorescent group such as phycoerythrin. The labeled nucleic acid is then incubated with the probes immobilized on the chip using a fluidics station. For example, Manz et al. (1993) Adv in Chromatogr. 1993; 33:1-66 describe the fabrication of fluidics devices and particularly microcapillary devices, in silicon and glass substrates.

Once the reaction is completed, the chip is inserted into a scanner and patterns of hybridization are detected. The hybridization data is collected, as a signal emitted from the reporter groups already incorporated into the nucleic acid, which is now bound to the probes attached to the chip. Since the sequence and position of each probe immobilized on the chip is known, the identity of the nucleic acid hybridized to a given probe can be determined.

It will be appreciated that when utilized along with automated equipment, the above described detection methods can be used to screen multiple samples for ferretin light chain variant detectable disease both rapidly and easily.

According to various preferred embodiments of the methods of the present invention, determining the presence and/or level of any specific nucleic or amino acid in a biological sample obtained from, for example, a patient is effected by any one of a variety of methods including, but not limited to, a signal amplification method, a direct detection method and detection of at least one sequence change.

The signal amplification methods according to various preferred embodiments of the present invention may amplify, for example, a DNA molecule or an RNA molecule. Signal amplification methods which might be used as part of the present invention include, but are not limited to PCR, LCR (LAR), Self-Sustained Synthetic Reaction (3SR/NASBA) or a Q-Beta (Qβ) Replicase reaction.

Peptides

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

Polypeptide products can be biochemically synthesized such as by employing standard solid phase techniques. Such methods include exclusive solid phase synthesis, partial solid phase synthesis methods, fragment condensation, classical solution synthesis. These methods are preferably used when the peptide is relatively short (i.e., 10 kDa) and/or when it cannot be produced by recombinant techniques (i.e., not encoded by a nucleic acid sequence) and therefore involves different chemistry.

Solid phase polypeptide synthesis procedures are well known in the art and further described by John Morrow Stewart and Janis Dillaha Young, Solid Phase Peptide Syntheses (2nd Ed., Pierce Chemical Company, 1984).

Synthetic polypeptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of a polypeptide are desired, it can be generated using recombinant techniques such as described by Bitter et al., (1987) Methods in Enzymol. 153: 516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

It will be appreciated that peptides identified according to the teachings of the present invention may be degradation products, synthetic peptides or recombinant peptides as well as peptidomimetics, typically, synthetic peptides and peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted by synthetic non-natural acid such as Phenylglycine, TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Table 1 below lists naturally occurring amino acids which can be used with the present invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid | Xaa | X |

Since the peptides of the present invention are preferably utilized in therapeutics which require the peptides to be in soluble form, the peptides of the present invention preferably include one or more non-natural or natural polar amino acids, including but not limited to serine and threonine which are capable of increasing peptide solubility due to their hydroxyl-containing side chain.

The peptides of the present invention are preferably utilized in a linear form, although it will be appreciated that in cases where cyclization does not severely interfere with peptide characteristics, cyclic forms of the peptide can also be utilized.

The peptides of the present invention can be biochemically synthesized such as by using standard solid phase techniques. These methods include exclusive solid phase synthesis, partial solid phase synthesis methods, fragment condensation, classical solution synthesis. These methods are preferably used when the peptide is relatively short (i.e., 10 kDa) and/or when it cannot be produced by recombinant techniques (i.e., not encoded by a nucleic acid sequence) and therefore involves different chemistry.

Solid phase peptide synthesis procedures are well known in the art and further described by John Morrow Stewart and Janis Dillaha Young, Solid Phase Peptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of the peptides of the present invention are desired, the peptides of the present invention can be generated using recombinant techniques such as described by Bitter et al., (1987) Methods in Enzymol. 153: 516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

Expression Systems

To enable cellular expression of the polynucleotides of the present invention, a nucleic acid construct according to the present invention may be used, which includes at least a coding region of one of the above nucleic acid sequences, and further includes at least one cis acting regulatory element. As used herein, the phrase "cis acting regulatory element" refers to a polynucleotide sequence, preferably a promoter, which binds a trans acting regulator and regulates the transcription of a coding sequence located downstream thereto.

Any suitable promoter sequence can be used by the nucleic acid construct of the present invention.

Preferably, the promoter utilized by the nucleic acid construct of the present invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166). The nucleic acid construct of the present invention can further include an enhancer, which can be adjacent or distant to the promoter sequence and can function in up regulating the transcription therefrom.

The nucleic acid construct of the present invention preferably further includes an appropriate selectable marker and/or an origin of replication. Preferably, the nucleic acid construct utilized is a shuttle vector, which can propagate both in E. coli (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus or an artificial chromosome.

Examples of suitable constructs include, but are not limited to, pcDNA3, pcDNA3.1 (±), pGL3, PzeoSV2 (±), pDisplay, pEF/myc/cyto, pCMV/myc/cyto each of which is commercially available from Invitrogen Co. (www.invitrogen.com). Examples of retroviral vector and packaging systems are those sold by Clontech, San Diego, Calif., including Retro-X vectors pLNCX and pLXSN, which permit cloning into multiple cloning sites and the transgene is transcribed from CMV promoter. Vectors derived from Mo-MuLV are also included such as pBabe, where the transgene will be transcribed from the 5'LTR promoter.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of the present invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Variant Recombinant Expression Vectors and Host Cells

Another aspect of the invention pertains to vectors, preferably expression vectors, containing a nucleic acid encoding a variant protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., variant proteins, mutant forms of variant proteins, fusion proteins, etc.).

The recombinant expression vectors of the invention can be designed for production of variant proteins in prokaryotic or eukaryotic cells. For example, variant proteins can be expressed in bacterial cells such as *Escherichia coli*, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, to the amino or C terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin, PreScission, TEV and enterokinase. Typical fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) Gene 69:301-315) and pET 11d (Studier et al., Gene Expression Technology: Methods in Enzymology 185, Academic Press, San Diego, Calif. (1990) 60-89)—not accurate, pET11a-d have N terminal T7 tag.

One strategy to maximize recombinant protein expression in *E. coli* is to express the protein in a host bacterium with an impaired capacity to proteolytically cleave the recombinant protein. See, e.g., Gottesman, Gene Expression Technology: Methods in Enzymology 185, Academic Press, San Diego, Calif. (1990) 119-128. Another strategy is to alter the nucleic acid sequence of the nucleic acid to be inserted into an expression vector so that the individual codons for each amino acid are those preferentially utilized in *E. coli* (see, e.g., Wada, et al., 1992. Nucl. Acids Res. 20: 2111-2118). Such alteration of nucleic acid sequences of the invention can be carried out by standard DNA synthesis techniques. Another strategy to solve codon bias is by using BL21-codon plus bacterial strains (Invitrogen) or Rosetta bacterial strain (Novagen), these strains contain extra copies of rare *E.coli* tRNA genes.

In another embodiment, the expression vector encoding for the variant protein is a yeast expression vector. Examples of vectors for expression in yeast *Saccharomyces cerivisae* include pYepSec1 (Baldari, et al., 1987. EMBO J. 6: 229-234), pMFa (Kurjan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.).

Alternatively, variant protein can be produced in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In yet another embodiment, a nucleic acid of the invention is expressed in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195), pIRESpuro (Clontech), pUB6 (Invitrogen), pCEP4 (Invitrogen) pREP4 (Invitrogen), pcDNA3 (Invitrogen). When used in mammalian cells, the expression vector's control functions are often provided by viral regulatory elements. For example, commonly used promoters are derived from polyoma, adenovirus 2, cytomegalovirus, Rous Sarcoma Virus, and simian virus 40. For other suitable expression systems for both prokaryotic and eukaryotic cells see, e.g., Chapters 16 and 17 of Sambrook, et al., Molecular Cloning: A Laboratory Manual. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Banerji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the alpha-fetoprotein promoter (Campes and Tilghman, 1989. Genes Dev. 3: 537-546).

The invention further provides a recombinant expression vector comprising a DNA molecule of the invention cloned into the expression vector in an antisense orientation. That is, the DNA molecule is operatively-linked to a regulatory sequence in a manner that allows for expression (by transcription of the DNA molecule) of an RNA molecule that is antisense to mRNA encoding for variant protein. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," Reviews-Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, variant protein can be produced in bacterial cells such as E. coli, insect cells, yeast, plant or mammalian cells (such as Chinese hamster ovary cells (CHO) or COS or 293 cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual. 2nd ed., Cold Spring Harbor Laboratory, Cold Spring Harbor Laboratory Press, Cold Spring Harbor, N.Y., 1989), and other laboratory manuals. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin, puromycin, blasticidin and methotrexate. Nucleic acids encoding a selectable marker can be introduced into a host cell on the same vector as that encoding variant protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) variant protein. Accordingly, the invention further provides methods for producing variant protein using the host cells of the invention. In one embodiment, the method comprises culturing the host cell of the present invention (into which a recombinant expression vector encoding variant protein has been introduced) in a suitable medium such that variant protein is produced. In another embodiment, the method further comprises isolating variant protein from the medium or the host cell.

For efficient production of the protein, it is preferable to place the nucleotide sequences encoding the variant protein under the control of expression control sequences optimized for expression in a desired host. For example, the sequences may include optimized transcriptional and/or translational regulatory sequences (such as altered Kozak sequences).

Protein Modifications

Fusion Proteins

A fusion protein may be prepared from a variant protein according to the present invention by fusion with a portion of an immunoglobulin comprising a constant region of an immunoglobulin. More preferably, the portion of the immunoglobulin comprises a heavy chain constant region which is optionally and more preferably a human heavy chain constant region. The heavy chain constant region is most preferably an IgG heavy chain constant region, and optionally and most preferably is an Fc chain, most preferably an IgG Fc fragment that comprises CH2 and CH3 domains. Although any IgG subtype may optionally be used, the IgG1 subtype is preferred. The Fc chain may optionally be a known or "wild type" Fc chain, or alternatively may be mutated. Non-limiting, illustrative, exemplary types of mutations are described in US Patent Application No. 20060034852, published on Feb. 16 2006, hereby incorporated by reference as if fully set forth herein. The term "Fc chain" also optionally comprises any type of Fc fragment.

Several of the specific amino acid residues that are important for antibody constant region-mediated activity in the IgG subclass have been identified. Inclusion, substitution or exclusion of these specific amino acids therefore allows for inclusion or exclusion of specific immunoglobulin constant region-mediated activity. Furthermore, specific changes may result in aglycosylation for example and/or other desired changes to the Fc chain. At least some changes may optionally be made to block a function of Fc which is considered to be undesirable, such as an undesirable immune system effect, as described in greater detail below.

Non-limiting, illustrative examples of mutations to Fc which may be made to modulate the activity of the fusion protein include the following changes (given with regard to the Fc sequence nomenclature as given by Kabat, from Kabat EA et al: Sequences of Proteins of Immunological Interest. US Department of Health and Human Services, NIH, 1991): 220C→S; 233-238 ELLGGP→EAEGAP; 265D→A, preferably in combination with 434N→A; 297N→A (for example to block N-glycosylation); 318-322 EYKCK→AYACA; 330-331AP→SS; or a combination thereof (see for example M. Clark, "Chemical Immunol and Antibody Engineering", pp 1-31 for a description of these mutations and their effect). The construct for the Fc chain which features the above changes optionally and preferably comprises a combination of the hinge region with the CH2 and CH3 domains.

The above mutations may optionally be implemented to enhance desired properties or alternatively to block non-desired properties. For example, aglycosylation of antibodies was shown to maintain the desired binding functionality while blocking depletion of T-cells or triggering cytokine release, which may optionally be undesired functions (see M. Clark, "Chemical Immunol and Antibody Engineering", pp 1-31). Substitution of 331proline for serine may block the ability to activate complement, which may optionally be considered an undesired function (see M. Clark, "Chemical Immunol and Antibody Engineering", pp 1-31). Changing 330alanine to serine in combination with this change may also enhance the desired effect of blocking the ability to activate complement.

Residues 235 and 237 were shown to be involved in antibody-dependent cell-mediated cytotoxicity (ADCC), such that changing the block of residues from 233-238 as described may also block such activity if ADCC is considered to be an undesirable function.

Residue 220 is normally a cysteine for Fc from IgG1, which is the site at which the heavy chain forms a covalent linkage with the light chain. Optionally, this residue may be changed to a serine, to avoid any type of covalent linkage (see M. Clark, "Chemical Immunol and Antibody Engineering", pp 1-31).

The above changes to residues 265 and 434 may optionally be implemented to reduce or block binding to the Fc receptor, which may optionally block undesired functionality of Fc related to its immune system functions (see "Binding site on Human IgG1 for Fc Receptors", Shields et al, vol 276, pp 6591-6604, 2001).

The above changes are intended as illustrations only of optional changes and are not meant to be limiting in any way. Furthermore, the above explanation is provided for descriptive purposes only, without wishing to be bound by a single hypothesis.

Addition of Groups

If a variant according to the present invention is a linear molecule, it is possible to place various functional groups at various points on the linear molecule which are susceptible to or suitable for chemical modification. Functional groups can be added to the termini of linear forms of the variant. In some embodiments, the functional groups improve the activity of the variant with regard to one or more characteristics, including but not limited to, improvement in stability, penetration (through cellular membranes and/or tissue barriers), tissue localization, efficacy, decreased clearance, decreased toxicity, improved selectivity, improved resistance to expulsion by cellular pumps, and the like. For convenience sake and without wishing to be limiting, the free N-terminus of one of the sequences contained in the compositions of the invention will be termed as the N-terminus of the composition, and the free C-terminal of the sequence will be considered as the C-terminus of the composition. Either the C-terminus or the N-terminus of the sequences, or both, can be linked to a carboxylic acid functional groups or an amine functional group, respectively.

Non-limiting examples of suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the active ingredient attached thereto into a cell, for example, by reducing the hydrophilicity and increasing the lipophilicity of the active ingredient, these being an example for "a moiety for transport across cellular membranes".

These moieties can optionally and preferably be cleaved in vivo, either by hydrolysis or enzymatically, inside the cell. (Ditter et al., J. Pharm. Sci. 57:783 (1968); Ditter et al., J. Pharm. Sci. 57:828 (1968); Ditter et al., J. Pharm. Sci. 58:557 (1969); King et al., Biochemistry 26:2294 (1987); Lindberg et al., Drug Metabolism and Disposition 17:311 (1989); and Tunek et al., Biochem. Pharm. 37:3867 (1988), Anderson et al., Arch. Biochem. Biophys. 239:538 (1985) and Singhal et al., FASEB J. 1:220 (1987)). Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a composition of the present invention is protected, preferably with a methyl, ethyl, benzyl or substituted benzyl ester, more preferably as a benzyl ester.

Non-limiting, illustrative examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include but are not limited to acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH3-O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—, Adamantan, naphtalen, myristoleyl, toluen, biphenyl, cinnamoyl, nitrobenzoy, toluoyl, furoyl, benzoyl, cyclohexane, norbomane, or Z-caproic. In order to facilitate the N-acylation, one to four glycine residues can be present in the N-terminus of the molecule.

The carboxyl group at the C-terminus of the compound can be protected, for example, by a group including but not limited to an amide (i.e., the hydroxyl group at the C-terminus is replaced with —NH2, —NHR2 and —NR2R3) or ester (i.e. the hydroxyl group at the C-terminus is replaced with —OR2). R2 and R3 are optionally independently an aliphatic, substituted aliphatic, benzyl, substituted benzyl, aryl or a substituted aryl group. In addition, taken together with the nitrogen atom, R2 and R3 can optionally form a C4 to C8 heterocyclic ring with from about 0-2 additional heteroatoms such as nitrogen, oxygen or sulfur. Non-limiting suitable examples of suitable heterocyclic rings include piperidinyl, pyrrolidinyl, morpholino, thiomorpholino or piperazinyl. Examples of C-terminal protecting groups include but are not limited to —NH2, —NHCH3, —N(CH3)2, —NH(ethyl), —N(ethyl)2, —N(methyl)(ethyl), —NH(benzyl), —N(C1-C4 alkyl)(benzyl), —NH(phenyl), —N(C1-C4 alkyl)(phenyl), —OCH3, —O-(ethyl), —O-(n-propyl), —O-(n-butyl), —O-(iso-propyl), —O-(sec-butyl), —O-(t-butyl), —O-benzyl and —O-phenyl.

Substitution by Peptidomimetic Moieties

A "peptidomimetic organic moiety" can optionally be substituted for amino acid residues in the composition of this invention both as conservative and as non-conservative substitutions. These moieties are also termed "non-natural amino acids" and may optionally replace amino acid residues, amino acids or act as spacer groups within the peptides in lieu of deleted amino acids. The peptidomimetic organic moieties optionally and preferably have steric, electronic or configurational properties similar to the replaced amino acid and such peptidomimetics are used to replace amino acids in the essential positions, and are considered conservative substitutions. However such similarities are not necessarily required. According to preferred embodiments of the present invention, one or more peptidomimetics are selected such that the composition at least substantially retains its physiological activity as compared to the native variant protein according to the present invention.

Peptidomimetics may optionally be used to inhibit degradation of the peptides by enzymatic or other degradative processes. The peptidomimetics can optionally and preferably be produced by organic synthetic techniques. Non-limiting examples of suitable peptidomimetics include D amino acids of the corresponding L amino acids, tetrazol (Zabrocki et al., J. Am. Chem. Soc. 110:5875-5880 (1988)); isosteres of amide bonds (Jones et al., Tetrahedron Lett. 29: 3853-3856 (1988)); LL-3-amino-2-propenidone-6-carboxylic acid (LL-Acp) (Kemp et al., J. Org. Chem. 50:5834-5838 (1985)). Similar analogs are shown in Kemp et al., Tetrahedron Lett. 29:5081-5082 (1988) as well as Kemp et al., Tetrahedron Lett. 29:5057-5060 (1988), Kemp et al., Tetrahedron Lett. 29:4935-4938 (1988) and Kemp et al., J. Org. Chem. 54:109-115 (1987). Other suitable but exemplary peptidomimetics are shown in Nagai and Sato, Tetrahedron Lett. 26:647-650 (1985); Di Maio et al., J. Chem. Soc. Perkin Trans., 1687 (1985); Kahn et al., Tetrahedron Lett. 30:2317 (1989); Olson et al., J. Am. Chem. Soc. 112:323-333 (1990); Garvey et al., J. Org. Chem. 56:436 (1990). Further suitable exemplary peptidomimetics include hydroxy-1,2,3,4-tetrahydroisoquinoline-3-carboxylate (Miyake et al., J. Takeda Res. Labs 43:53-76 (1989)); 1,2,3,4-tetrahydro-isoquinoline-3-carboxylate (Kazmierski et al., J. Am. Chem. Soc. 133:2275-2283 (1991)); histidine isoquinolone carboxylic acid (HIC) (Zechel et al., Int. J. Pep. Protein Res. 43 (1991)); (2S, 3S)-methyl-phenylalanine, (2S, 3R)-methyl-phenylalanine, (2R, 3S)-methyl-phenylalanine and (2R, 3R)-methyl-phenylalanine (Kazmierski and Hruby, Tetrahedron Lett. (1991)).

Exemplary, illustrative but non-limiting non-natural amino acids include beta-amino acids (beta3 and beta2), homo-amino acids, cyclic amino acids, aromatic amino acids, Pro and Pyr derivatives, 3-substituted Alanine derivatives, Glycine derivatives, ring-substituted Phe and Tyr Derivatives, linear core amino acids or diamino acids. They are available from a variety of suppliers, such as Sigma-Aldrich (USA) for example.

Chemical Modifications

In the present invention any part of a variant protein may optionally be chemically modified, i.e. changed by addition of functional groups. For example the side amino acid residues appearing in the native sequence may optionally be modified, although as described below alternatively other part(s) of the protein may optionally be modified, in addition to or in place of the side amino acid residues. The modification may optionally be performed during synthesis of the molecule if a chemical synthetic process is followed, for example by adding a chemically modified amino acid. However, chemical modification of an amino acid when it is already present in the molecule ("in situ" modification) is also possible.

The amino acid of any of the sequence regions of the molecule can optionally be modified according to any one of the following exemplary types of modification (in the peptide conceptually viewed as "chemically modified"). Non-limiting exemplary types of modification include carboxymethylation, acylation, phosphorylation, glycosylation or fatty acylation. Ether bonds can optionally be used to join the serine or threonine hydroxyl to the hydroxyl of a sugar. Amide bonds can optionally be used to join the glutamate or aspartate carboxyl groups to an amino group on a sugar (Garg and Jeanloz, Advances in Carbohydrate Chemistry and Biochemistry, Vol.43, Academic Press (1985); Kunz, Ang. Chem. Int. Ed. English 26:294-308 (1987)). Acetal and ketal bonds can also optionally be formed between amino acids and carbohydrates. Fatty acid acyl derivatives can optionally be made, for example, by acylation of a free amino group (e.g., lysine) (Toth et al., Peptides: Chemistry, Structure and Biology, Rivier and Marshal, eds., ESCOM Publ., Leiden, 1078-1079 (1990)).

As used herein the term "chemical modification", when referring to a protein or peptide according to the present invention, refers to a protein or peptide where at least one of its amino acid residues is modified either by natural processes, such as processing or other post-translational modifications, or by chemical modification techniques which are well known in the art. Examples of the numerous known modifications typically include, but are not limited to: acetylation, acylation, amidation, ADP-ribosylation, glycosylation, GPI anchor formation, covalent attachment of a lipid or lipid derivative, methylation, myristylation, pegylation, prenylation, phosphorylation, ubiquitination, or any similar process.

Other types of modifications optionally include the addition of a cycloalkane moiety to a biological molecule, such as a protein, as described in PCT Application No. WO 2006/050262, hereby incorporated by reference as if fully set forth herein. These moieties are designed for use with biomolecules and may optionally be used to impart various properties to proteins.

Furthermore, optionally any point on a protein may be modified. For example, pegylation of a glycosylation moiety on a protein may optionally be performed, as described in PCT Application No. WO 2006/050247, hereby incorporated by reference as if fully set forth herein. One or more polyethylene glycol (PEG) groups may optionally be added to O-linked and/or N-linked glycosylation. The PEG group may optionally be branched or linear. Optionally any type of water-soluble polymer may be attached to a glycosylation site on a protein through a glycosyl linker.

Altered Glycosylation

Variant proteins of the invention may be modified to have an altered glycosylation pattern (i.e., altered from the original or native glycosylation pattern). As used herein, "altered" means having one or more carbohydrate moieties deleted, and/or having at least one glycosylation site added to the original protein.

Glycosylation of proteins is typically either N-linked or O-linked. N-linked refers to the attachment of the carbohydrate moiety to the side chain of an asparagine residue. The tripeptide sequences, asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to variant proteins of the invention is conveniently accomplished by altering the amino acid sequence of the protein such that it contains one or more of the above-described tripeptide sequences (for N-linked glycosylation sites). The alteration may also be made by the addition of, or substitution by, one or more serine or threonine residues in the sequence of the original protein (for O-linked glycosylation sites). The protein's amino acid sequence may also be altered by introducing changes at the DNA level.

Another means of increasing the number of carbohydrate moieties on proteins is by chemical or enzymatic coupling of glycosides to the amino acid residues of the protein. Depending on the coupling mode used, the sugars may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in Aplin and Wriston, CRC Crit. Rev. Biochem., 22: 259-306 (1981).

Removal of any carbohydrate moieties present on variant proteins of the invention may be accomplished chemically or enzymatically. Chemical deglycosylation requires exposure of the protein to trifluoromethanesulfonic acid, or an equivalent compound. This treatment results in the cleavage of most or all sugars except the linking sugar (N-acetylglucosamine or N-acetylgalactosamine), leaving the amino acid sequence intact.

Chemical deglycosylation is described by Hakimuddin et al., Arch. Biochem. Biophys., 259: 52 (1987); and Edge et al., Anal. Biochem., 118: 131 (1981). Enzymatic cleavage of carbohydrate moieties on proteins can be achieved by the use of a variety of endo- and exo-glycosidases as described by Thotakura et al., Meth. Enzymol., 138: 350 (1987).

Methods of Treatment

As mentioned hereinabove the novel therapeutic protein variants of the present invention and compositions derived therefrom (i.e., peptides, oligonucleotides) can be used to treat cluster, variant or protein-related diseases, disorders or conditions.

Thus, according to an additional aspect of the present invention there is provided a method of treating cluster, variant or protein-related disease, disorder or condition in a subject.

The subject according to the present invention is a mammal, preferably a human which is diagnosed with one of the disease, disorder or conditions described hereinabove, or alternatively is predisposed to at least one type of the cluster, variant or protein-related disease, disorder or conditions described hereinabove.

As used herein the term "treating" refers to preventing, curing, reversing, attenuating, alleviating, minimizing, suppressing or halting the deleterious effects of the above-described diseases, disorders or conditions.

Treating, according to the present invention, can be effected by specifically upregulating the expression of at least one of the polypeptides of the present invention in the subject.

Optionally, upregulation may be effected by administering to the subject at least one of the polypeptides of the present invention (e.g., recombinant or synthetic) or an active portion thereof, as described herein. However, since the bioavailability of large polypeptides may potentially be relatively small due to high degradation rate and low penetration rate, administration of polypeptides is preferably confined to small peptide fragments (e.g., about 100 amino acids). The polypeptide or peptide may optionally be administered in as part of a pharmaceutical composition, described in more detail below.

It will be appreciated that treatment of the above-described diseases according to the present invention may be combined with other treatment methods known in the art (i.e., combination therapy). Thus, treatment of malignancies using the agents of the present invention may be combined with, for example, radiation therapy, antibody therapy and/or chemotherapy.

Alternatively or additionally, an upregulating method may optionally be effected by specifically upregulating the amount (optionally expression) in the subject of at least one of the polypeptides of the present invention or active portions thereof.

As is mentioned hereinabove and in the Examples section which follows, the biomolecular sequences of this aspect of the present invention may be used as valuable therapeutic tools in the treatment of diseases, disorders or conditions in which altered activity or expression of the wild-type gene product (known protein) is known to contribute to disease, disorder or condition onset or progression. For example, in case a disease is caused by overexpression of a membrane bound-receptor, a soluble variant thereof may be used as an antagonist which competes with the receptor for binding the ligand, to thereby terminate signaling from the receptor. Examples of such diseases are listed in the Examples section which follows.

Pharmaceutical Compositions and Delivery thereof

The present invention features a pharmaceutical composition comprising a therapeutically effective amount of a therapeutic agent according to the present invention, which is preferably a therapeutic protein variant as described herein. Optionally and alternatively, the therapeutic agent could be an antibody or an oligonucleotide that specifically recognizes and binds to the therapeutic protein variant, but not to the corresponding full length known protein.

According to the present invention the therapeutic agent could be any one of novel MCP-1 variant polypeptides and polynucleotides of the present invention. Optionally and alternatively, the therapeutic agent could be an antibody or an oligonucleotide that specifically recognizes and binds to the novel MCP-1 variant polypeptides and polynucleotides of the present invention.

According to the present invention the therapeutic agent could be used for the treatment or prevention of a wide range of diseases, as described in greater detail below.

Alternatively, the pharmaceutical composition of the present invention includes a therapeutically effective amount of at least an active portion of a therapeutic protein variant polypeptide.

The pharmaceutical composition according to the present invention is preferably used for the treatment of cluster-related (variant-related) diseases, which includes but is not limited to diseases wherein MCP-1 is involved in the etiology or pathogenesis of the disease process as described herein.

"Treatment" refers to both therapeutic treatment and prophylactic or preventative measures. Those in need of treatment include those already with the disorder as well as those in which the disorder is to be prevented. Hence, the mammal to be treated herein may have been diagnosed as having the disorder or may be predisposed or susceptible to the disorder. "Mammal" for purposes of treatment refers to any animal classified as a mammal, including humans, domestic and farm animals, and zoo, sports, or pet animals, such as dogs, horses, cats, cows, etc. Preferably, the mammal is human.

A "disorder" is any condition that would benefit from treatment with the agent according to the present invention. This includes chronic and acute disorders or diseases including those pathological conditions which predispose the mammal to the disorder in question.

The term "therapeutically effective amount" refers to an amount of agent according to the present invention that is effective to treat a disease or disorder in a mammal.

The therapeutic agents of the present invention can be provided to the subject per se, or as part of a pharmaceutical composition where they are mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the preparation accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections. Alternately, one may administer a preparation in a local rather than systemic manner, for example, via injection of the preparation directly into a specific region of a patient's body.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Pharmaceutical compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Diagnostic Methods

The term "marker" in the context of the present invention refers to a nucleic acid fragment, a peptide, or a polypeptide, which is differentially present in a sample taken from patients having or predisposed to an MCP-1-related disease, disorder or condition as compared to a comparable sample taken from subjects who do not have a such a disease, disorder or condition.

According to the present invention the marker could be any one of novel MCP-1 variant polypeptides and polynucleotides of the present invention. Optionally and alternatively, the marker could be an antibody or an oligonucleotide that specifically recognizes and binds to the novel MCP-1 variant polypeptides and polynucleotides of the present invention.

According to the present invention the marker could be used for the diagnosis, prognosis, prediction, screening, early diagnosis, determination of progression, therapy selection and treatment monitoring of a wide range of diseases, as described in greater detail below.

Typically the level of the marker in a biological sample obtained from the subject is different (i.e., increased or decreased) from the level of the same variant in a similar sample obtained from a healthy individual.

In another embodiment, this invention provides antibodies specifically recognizing the splice variants and polypeptide fragments thereof of this invention. Preferably such antibodies differentially recognize splice variants of the present invention but do not recognize a corresponding known protein (such known proteins are discussed with regard to their splice variants in the Examples below).

In another embodiment, this invention provides a method for detecting a splice variant according to the present invention in a biological sample, comprising: contacting a biological sample with an antibody specifically recognizing a splice variant according to the present invention under conditions whereby the antibody specifically interacts with the splice variant in the biological sample but do not recognize known corresponding proteins (wherein the known protein is discussed with regard to its splice variant(s) in the Examples below), and detecting the interaction; wherein the presence of an interaction correlates with the presence of a splice variant in the biological sample.

In another embodiment, this invention provides a method for detecting a splice variant nucleic acid sequences in a biological sample, comprising: hybridizing the isolated nucleic acid molecules or oligonucleotide fragments of at least about a minimum length to a nucleic acid material of a biological sample and detecting a hybridization complex; wherein the presence of a hybridization complex correlates with the presence of a splice variant nucleic acid sequence in the biological sample.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Description for Cluster S71513

Cluster S71513 features 1 transcript, S71513_T1 (SEQ ID NO:1) and 5 segments of interest, S71513_N0 (SEQ ID NO:2); S71513_N1 (SEQ ID NO:3); S71513_N4 (SEQ ID NO:4); S71513_N5 (SEQ ID NO:5); and S71513_N6 (SEQ ID NO:6). The transcript S71513_T1 (SEQ ID NO:1) encodes a variant protein S71513_P1 (SEQ ID NO:9).

These sequences are variants of the known protein Small inducible cytokine A2 precursor ((SEQ ID NO:8) SwissProt accession identifier SY02_HUMAN; known also according to the synonyms CCL2; Monocyte chemotactic protein 1; MCP-1; Monocyte chemoattractant protein-1; Monocyte chemotactic and activating factor; MCAF; Monocyte secretory protein JE; HC11), referred to herein as the previously known protein.

The amino acid sequence comparison between MCP1-65 (SEQ ID NO: 9; S71513_P1) and the known MCP1-WT (SEQ ID NO: 8; NP_002973) is shown in FIG. 1a. The comparison report between S71513_P1 and SY02_HUMAN (NP_002973) is given below:

An isolated chimeric polypeptide encoding for S71513_P1 (SEQ ID NO:9), comprising a first amino acid sequence being at least 90% and preferably at least 95% homologous to MKVSAALLCLLLIAATFIPQGLAQP-DAINAPVTCCYNFTNRKISVQRLASYRRITS SKCP-KEAV corresponding to amino acids 1-64 of SY02_HUMAN (SEQ ID NO:8), which also corresponds to amino acids 1-64 of S71513_P1 (SEQ ID NO:9), and an amino acid M corresponding to amino acid 65 of S71513_P1 (SEQ ID NO:9), wherein said first amino acid sequence and said amino acid are contiguous and in a sequential order.

The comparison of the precursor and the processed MCP-1-65 variant to the precursor and the processed wild type MCP-1 is shown in Table 2 below.

TABLE 2

```
Unprocessed*
MKVSAALLCL LLIAATFIPQ GLAQPDAINA PVTCCYNFTN

Processed**
.................... QPDAINA PVTCCYNFTN

MCP-1-65
MKVSAALLCL LLIAATFIPQ GLAQPDAINA PVTCCYNFTN pMCP-1-65***
.................... QPDAINA PVTCCYNFTN

Unprocessed*
RKISVQRLAS YRRITSSKCP KEAVIFKTIV AKEICADPKQ

Processed**
RKISVQRLAS YRRITSSKCP KEAVIFKTIV AKEICADPKQ

MCP-1-65
RKISVQRLAS YRRITSSKCP KEAVM...............

pMCP-1-65***
RKISVQRLAS YRRITSSKCP KEAVM...............

Unprocessed*
KWVQDSMDHL DKQTQTPKT
```

TABLE 2-continued

```
Processed**
KWVQDSMDHL DKQTQTPKT

MCP-1-65
....................

pMCP-1-65***
....................
```

*NCBI Accession No. 002703
**Rollins et al. Molecular and Cellular Biology, 9(11):4687-4695, 1989 and U.S. Pat. No. 5,459,128
***processed MCP-1-65

The localization of the variant protein was determined according to results from a number of different software programs and analyses, including analyses from SignalP and other specialized programs. The variant protein is believed to be located as follows with regard to the cell: secreted.

Variant protein S71513_P1 (SEQ ID NO:9) also has the following non-silent SNPs (Single Nucleotide Polymorphisms) as listed in Table 3, (given according to their positions on the amino acid sequence, with the alternative amino acids listed; the last column indicates whether the SNP is known or not; the presence of known SNPs in variant protein S71513_P1 (SEQ ID NO:9) sequence provides support for the deduced sequence of this variant protein according to the present invention).

TABLE 3

| Amino acid mutations | | |
|---|---|---|
| SNP position(s) on amino acid sequence | Alternative amino acid(s) | Previously known SNP? |
| 15 | A -> | No |
| 15 | A -> G | No |
| 22 | L -> P | No |

The glycosylation sites of variant protein S71513_P1 (SEQ ID NO:9), as compared to the known protein Small inducible cytokine A2 precursor, are described in Table 4 (given according to their positions on the amino acid sequence in the first column; the second column indicates whether the glycosylation site is present in the variant protein; and the last column indicates whether the position is different on the variant protein).

TABLE 4

| Glycosylation site(s) | | |
|---|---|---|
| Position(s) on known amino acid sequence | Present in variant protein? | Position(s) on variant protein |
| 37 | Yes | 37 |

The phosphorylation sites of variant protein S71513_P1 (SEQ ID NO:9), as compared to the known protein, are described in Table 5 (given according to their positions on the amino acid sequence in the first column; the second column indicates whether the phosphorylation site is present in the variant protein; and the last column indicates whether the position is different on the variant protein).

TABLE 5

| Phosphorylation site(s) | | |
|---|---|---|
| Position(s) on known amino acid sequence | Present in variant protein? | Position(s) on variant protein |
| 24 | Yes | 24 |

The variant protein has the following domains, as determined by using InterPro. The domains are described in Table 6:

TABLE 6

| InterPro domain(s) | | |
|---|---|---|
| Domain description | Analysis type | Position(s) on protein |
| Small chemokine, interleukin-8-like | HMMPfam | 24-65 |
| Small chemokine, interleukin-8-like | ProfileScan | 1-65 |

The coding portion of S71513_T1 (SEQ ID NO:1) transcript, encoding the S71513_P variant (SEQ ID NO:9), starts at position 341 and ends at position 535 of the transcript S71513_T1 (SEQ ID NO:1). The transcript also has the following SNPs as listed in Table 7 (given according to their position on the nucleotide sequence, with the alternative nucleic acid listed; the last column indicates whether the SNP is known or not; the presence of known SNPs in variant protein S71513_P1 (SEQ ID NO:9) sequence provides support for the deduced sequence of this variant protein according to the present invention).

TABLE 7

| Nucleic acid SNPs | | |
|---|---|---|
| SNP Position(s) on nucleotide sequence | Alternative nucleic acid(s) | Previously known SNP |
| 219 | G -> T | Yes |
| 222 | C -> T | Yes |
| 383 | G -> | No |
| 384 | C -> G | No |
| 384 | C -> | No |
| 405 | T -> C | No |
| 445 | T -> C | Yes |
| 559 | C -> T | Yes |
| 963 | A -> G | No |
| 1087 | C -> T | Yes |
| 1110 | T -> | No |
| 1127 | A -> | No |
| 1203 | T -> G | No |
| 1203 | T -> | No |
| 1247 | C -> T | Yes |
| 1258 | C -> | No |
| 1306 | T -> | No |
| 1357 | T -> | No |

Example 2

Cloning and Expression of MCP-1 Variants

This example relates to the cloning and expression of MCP-1 variants according to the present invention. The following MCP-1 variants were selected: MCP-1_99 (wild type) (SEQ ID NOS:10, 11); MCP-1_92_7ND (positive control) (SEQ ID NOS:12, 13); MCP-1_65 Fc variant of present invention (SEQ ID NOS:14, 15).

FIG. 1b shows the schematic mRNA and protein structure of MCP-1. "WT 99aa" represents the known MCP-1 (SEQ ID NO:8). "65aa" represents the MCP-1 splice variant of the present invention, SEQ ID NO:9. "Antagonist (deletion 2-8 of mature) represents the known MCP-1-92-7ND (SEQ ID NO:25). Exons are represented by boxes with upper left to lower right fill, while introns are represented by two headed arrows. Proteins are shown in boxes with upper right to lower left fill. The unique regions are represented by white boxes.

Cloning of MCP-1 Variants:

The MCP-1 variant sequences were codon optimized to boost protein expression in mammalian system, as demonstrated in FIG. 2 and below. The optimized genes were synthesized by Blue Heron (USA) by using their proprietary gene synthesis technology with the addition of DNA sequences encoding the StrepII and His tags at the 3' of the WT MCP1_99 (SEQ ID Nos: 10,11) and the mutated MCP1 92 7ND (SEQ ID NOS: 12,13). The optimized sequences were cloned into EcoRI-NotI sites of pIRESpuro3. C-terminal deglycosylated Fc fragment was attached to extend the MCP-1-65 variant in order to increase the efficiency of expression, production and purification of MCP-1-65. The addition of sequence encoding the mutated human Fc IgG1 fragment (SEQ ID NO: 19) to the 3' of MCP-1-65 variant was obtained as follows: optimized DNA sequence of human mutated Fc (N297A) IgG1 (SEQ ID NO:18) was PCR amplified using the mut Fc optimized sequence as a template and the forward primer "3'MCP1 SpeI-5'Fc" (SEQ ID NO:17) and "IVS Rev2" (SEQ ID NO:16) reverse primer. The PCR amplification was carried under the following conditions: the reaction mix contained 5ul—X10 reaction buffer; 20 ng-mut Fc DNA template; 1 ul-dNTPs (10 mM each); 1 ul—platinum PFX DNA polymerase (Promega 11708039); 39 ul—H2O; and 1 ul—of each primer (10 µM) in a total reaction volume of 50 µl; the reaction conditions were as follows: 3 min at 94° C. followed by 30 cycles of: 30 seconds at 94° C. 30 seconds at 55° C. and 1 minute at 68° C.; followed by 10 minutes at 68° C. The PCR product was digested with SpeI and NotI and the insert was purified. Next, MCP1_65 Strep His pIRESpuro3 was digested with EcoRI and SpeI and a 174 bp fragment was eluted from an agarose gel. The digested PCR product, together with the 174 bp fragment, was ligated into pIRESpuro3, previously digested with EcoRI and NotI. Positive colonies were further sequence analyzed in order to rule out point mutations due to the PCR.

The optimized sequences are shown in FIG. 2. FIG. 2 shows the optimized nucleotide sequences of MCP-1 variants prepared for cloning in the expression vector pIRESpuro3, and their respective protein sequences. DNA sequences in bold show the relevant ORFs (open reading frames). FIG. 2A shows MCP1-99 nucleotide and protein sequences, SEQ ID NOS: 10 and 11, respectively. The Strep-His tag is underlined. FIG. 2B shows MCP1-92-7ND nucleotide and protein sequences, SEQ ID NOS: 12 and 13, respectively. The Strep-His tag is underlined. FIG. 2C shows MCP1-65 Fc nucleotide and protein sequences, SEQ ID NOS: 14 and 15, respectively. The Fc sequence is underlined. N297A mutation creating the non-glycosilated Fc mutant is shown in Italic.

FIG. 3 shows a schematic map of polynucleotide coding for MCP-1-65-Fc Mut (SEQ ID NO: 14) in the pIRESpuro3 expression vector, as described above.

Transfection of MCP-1 Constructs

The MCP-1 constructs were transfected into HEK-293T cells (ATCC #CRL-11268) as follows. One day prior to transfection, one well from a 6 well plate was plated with 500,000 cells in 2 ml DMEM. At the day of transfection, the FuGENE 6 Transfection Reagent (Roche, Cat#: 1-814-443) was warmed to ambient temperature and mixed prior to use. 6 μl of FuGENE Reagent were diluted into 100 μl DMEM (Dulbecco's modified Eagle's medium; Biological Industries, Cat#: 01-055-1A). Next, 2 micrograms of construct DNA were added. The contents were gently mixed and incubated at room temperature (RT) for 15 minutes. 100 μl of the complex mixture was added dropwise to the cells and swirled. The cells were incubated overnight at 37° C. with 5% $CO_2$. Following about 48 h, transfected cells were split and subjected to antibiotic selection with 5 microgram/ml puromycin. The surviving cells were propagated for about three weeks.

Expression Analysis

MCP-1 stable pools were analyzed by Western blot analysis using anti His and anti IgG antibodies. The supernatant of the puromycin resistant cells expressing the MCP1-65 Fc recombinant proteins were collected and were bound to protein A beads as follows. 50 ul Protein A sepharose (Amersham cat#17-5280-04) was washed twice with water and twice with 100 mM Tris pH 7.4. The beads were centrifuged for 2 min in 5500×g. Next, 1 ml of sample was loaded on the beads, and the sample was gently shaken for 45 min. at RT. Then, the beads were spun down and washed with 100 mM Tris pH 7.4, and the proteins were eluted with 50 ul SDS sample containing 100 mM Citrate Phosphate pH 3.5. The eluted proteins were incubated for 3 min, at 100° C. and loaded on a 12% SDS-PAGE gel.

The supernatant of the puromycin resistant cells expressing the MCP1-99 and MCP1-92__7ND recombinant proteins were collected and concentrated by 25 folds using cold TCA (Tri Chloroacetic Acid-SIGMA T9159). Supernatant concentration was done as follows: to each 750 microliter of supernatant 100 microliter of TCA was added and the samples were incubated for 5 minutes at minus 20° C. and 15 minutes at 4° C. the samples were then centrifuged for 15 minutes at 10,000×g and the pellet was resuspended in 30 microliter of 1*SDS sample buffer. The samples were then incubated for 3 minutes at 100° C. and loaded on a 18% SDS-PAGE gel.

Following electrophoresis, proteins on the gel were transferred to nitrocellulose membranes for 60 min at 35V using Invitrogen's transfer buffer and X-Cell II blot module. Following transfer, the blots were blocked with 5% skim milk in wash buffer (0.05% Tween-20 in PBS) for at least 60 minutes at room temperature with shaking. Following blocking, the blots were incubated for 60 min at room temperature with a commercially available anti IgG HRP antibody (SIGMA, Cat#A0170) or mouse anti Histidine Tag, (Serotec, Cat#: MCA1396) diluted in ⅕ blocking buffer, followed by washing with wash buffer. Next, the blot incubated with anti IgG was immersed in ECL solution (Enhanced Chemiluminescence) and detection was performed according to the manufacturer's instructions (Amersham; Cat #RPN2209), while the blots incubated with anti His were washed again with wash buffer and incubated 1 hour at room temperature with the secondary antibody Goat anti Mouse HRP, (Jackson, Cat#: 115-035-146) diluted in ⅕ blocking buffer, then the blots were washed and subjected to ECL detection as described above.

Figures 4B, 4C:
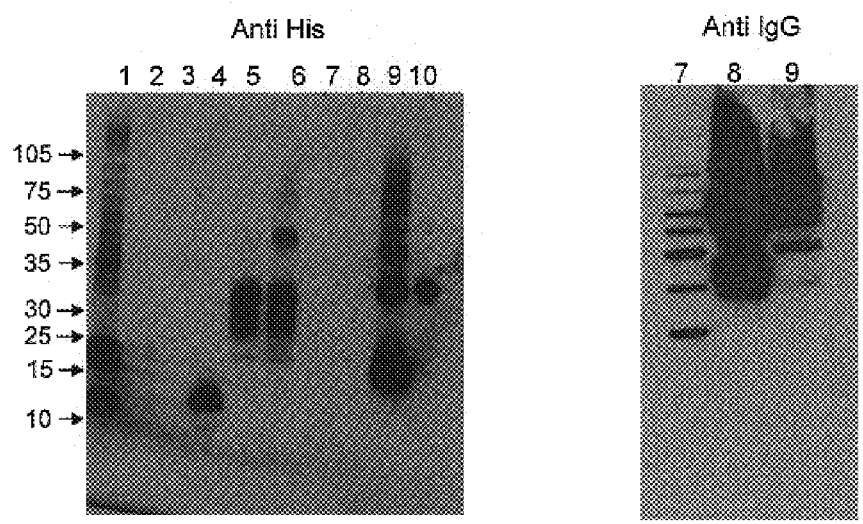
FIG. 4B demonstrates the MCP-1-92-7ND (SEQ ID NO:13) expression, using anti His antibodies. Lane 1 represents Molecular weight marker (Rainbow AMERSHAM RPN800); lane 9 represents MCP-1-92-7ND; lane 10 represents His control (~100 ng).
FIG. 4C demonstrates the MCP-1-m65-Fc (SEQ ID NO:15) expression, using anti IgG antibodies. Lane 7 represents molecular weight markers (MagicMark LC5602); lane 8 represents MCP-1-m65-Fc; lane 9 represents Fc control (~100 ng).

The Western blot results, demonstrating stable MCP-1 expression, are shown in FIG. 4. FIG. 4A demonstrates FIG. 4 shows Western blot analysis, demonstrating stable MCP-1 expression. FIG. 4A demonstrates the MCP-1-99 (SEQ ID NO: 11) expression, using anti His antibodies. Lane 1 represents Molecular weight marker (Rainbow AMERSHAM RPN800); lane 2 represents mock pIRESpuro3; lane 5 represents MCP-1-99 (SEQ ID NO: 11); lane 7 represents His control (~100 ng). FIG. 4B demonstrates the MCP-1-92-7ND (SEQ ID NO:13) expression, using anti His antibodies. Lane 1 represents Molecular weight marker (Rainbow AMERSHAM RPN800); lane 9 represents MCP-1-92-7ND; lane 10 represents His control (~100 ng). FIG. 4C demonstrates the MCP-1-65-Fc (SEQ ID NO:15) expression, using anti IgG antibodies. Lane 7 represents molecular weight markers (MagicMark LC5602); lane 8 represents MCP-1-65-Fc; lane 9 represents Fc control (~100 ng).

Example 3

MCP-1 Variant Protein Production and Purification

Description of Propagation Process

In order to produce sufficient amounts of the proteins, cells expressing MCP1-65-Fc-mut, MCP1-92-7ND and MCP1-99 WT were propagated to a final volume of 2000 ml. When the cells reached a density of about 2.7×106 cells/ml, the cultures were harvested by centrifugation and the sup filtered through a 0.22 um filter and used for protein purification. Harvested culture medium was concentrated approximately 5-10 fold and filtered through a 0.22 um filter.

Purification

MCP1-99-His-tag (WT) and MCP1-92-7ND-His-tag labeled proteins according to the present invention were purified by affinity chromatography using Ni-NTA resin, according to the following protocol. The supernatent was prepared as previously described and transferred to 3×250 ml centrifuge tubes. Six ml of Ni-NTA Superflow beads (Ni-NTA Superflow®, QIAGEN) were equilibrated with 10 column volumes of WFI (Teva Medical #AWF7114) and 10 column volumes of Buffer A (50 mM $NaH_2PO_4$, 300 mM NaCl, 10 mM imidazole, pH 8.0). The beads were added to the filtered supernatant, and the tube was incubated overnight on a rocking platform at 4 oC. The Ni-NTA beads in the 3×250 ml centrifuge tube were separated from the supernatant and packed in a 6 ml column of Ni-NTA Superflow. Beads were washed with buffer A at a flow rate of 1 column volume per minute, until O.D280 nm was lower than 0.01 mAU. Next, 1 ml Strep-Tactin Superflow beads were equilibrated with 10 CVs (column volumes) of WFI buffer (Teva Medical #AWF7114) and 10 column volumes of Buffer A (50 mM $NaH_2PO_4$, 300 mM NaCl, 10 mM imidazole, pH 8.0). The protein was eluted from the Ni-NTA beads with buffer B (50 mM $NaH_2PO_4$, 300 mM NaCl, 250 mM imidazole, pH 8.0) at a flow rate not higher than 1 ml/min and entered to the Step-Tactin column. Once the protein was washed from the Ni-NTA beads, the column was disconnected. The Strep-Tactin column was then washed with Buffer A, at a flow rate of 1 CV/min, with at least 5 CVs, until O.D280 nm was less then 0.01 mAU. The protein was eluted from the Strep-Tactin column with Strep-Tactin Elution Buffer (Buffer C; 50 mM $NaH_2PO_4$, 300 mM NaCl, 10 mM imidazole, 2.5 mM desthiobiotin, pH 8.0) at 0.2 ml per minute. Imidazole was removed from the purified protein by dialysis against 1×PBS (Dulbecco's Phosphate Buffered Saline, concentrated ten times, Biological Industries, Cat #020235A) at 4° C.

MCP1-65-Fc was purified using affinity chromatography with Protein A. The starting culture supernatant (sup) containing the MCP1-65-Fc was pH adjusted to 7.4 with 2M Tris-HCl pH 8.5 (approximately 2.5% of the final volume), and filtered through 0.22 μm filter. 1 ml nProtein-A sepharose previously equilibrated with 10 CV of buffer B (100 mM Citrate-Phosphate, pH 3.5) and 15 CV of buffer A (100 mM Tris.HCl, pH 7.5) was added to the sup and incubated overnight on a rolling platform at 4° C. The next day, 0.5/5 cm column was packed with the beads. The packed Protein-A column was connected to the FPLC AKTA at the "Wash Unbound" stage, at the program: "Protein A 1 ml Fc Purification". Wash was carried out with buffer A—up to 80 CV until O.D280 nm is lower than 0.01 mAU. The elution step was performed with buffer B. The protein was expected to elute in up to 5 CV, represented as the peak of the chromatography. Elution was collected in 1 ml fractions and pH of the elution was immediately (within 5 min) neutralized with addition of 1/10 volume of buffer C (2M Tris, pH 8.5) to each elution fraction tube. The column was regenerated and stored according to the manufacturer's instructions. Collected elution fractions were analyzed by SDS-PAGE to identify the protein-rich fractions (NuPage Bis-Tris 12% gels, MES-SDS Running buffer). SDS-PAGE was followed by Coomassie staining (Simply Blue SafeStain—Invitrogen; results not shown).

Fractions containing the protein (analyzed by SDS-PAGE) were pooled and dialyzed twice against 5L buffer D (1×PBS) 4-18 hrs each time, using Dialysis Membrane cassette, 10 kDa cutoff (PIERCE). BSA was added to a final concentration of 0.1% and the purified proteins were dialyzed extensively against PBS, filtered through sterile 0.45 μm PVDF filter and divided into sterile low binding Eppendorf tubes.

Purified Product Analysis

The MW, concentration and purity of the final products were analyzed by Bioanalyser according to manufacturer instructions. The results are summarized in Table 8 below.

TABLE 8

| Variant | Peak No | Purity | Concentration |
|---|---|---|---|
| MCP1-99 [WT] | 6 | 76.2 | 807 |
| MCP1-92 [7ND] | 4 | 95 | 758 |
| MCP1-65-Fc | 8 + 10 | 94.6 | 791 |

Figures 5A, 5B, 5C:
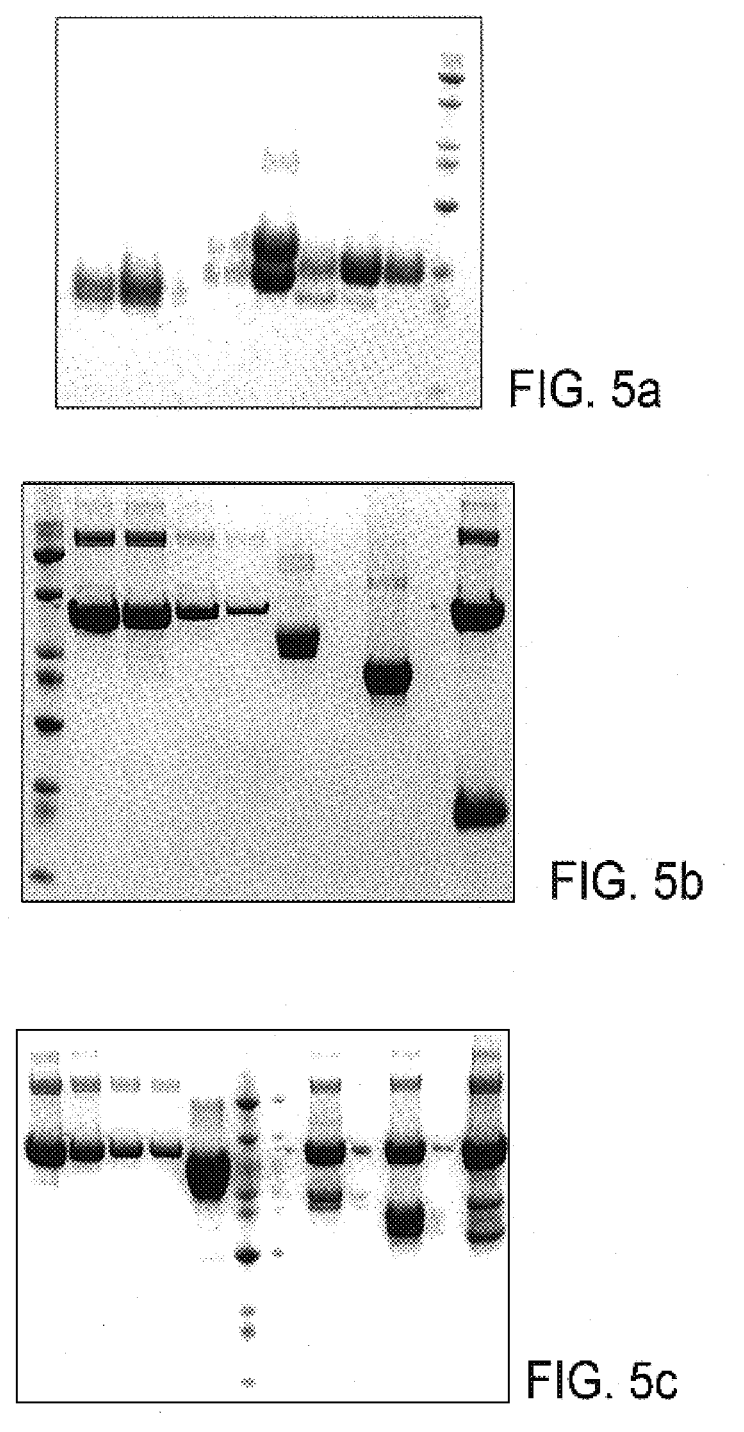

Quantitative SDS-PAGE was performed including 4 concentrations of BSA standards (100, 500, 1000, 2000 μg/ml). FIGS. 5A-C demonstrate the COOMASSIE staining results of SDS-PAGE gel of MCP-1 variants. FIG. 5A demonstrates the SDS-PAGE results of the MCP-1-99; FIG. 5B demonstrates SDS-PAGE results of MCP-1-92-7ND; FIG. 5C demonstrates SDS-PAGE results of MCP-1-65m-Fc. Tables 9-11 describe the samples loaded in each lane of the SDS-PAGE. In all cases the analysis was carried out on proteins after dialysis using 4-12% BT SDS-PAGE.

TABLE 9

SDS-PAGE of MCP-1-99

| lanes DS- | SAMPLE | Sample Vol. | 3XS.B with DTT | Loading Vol. |
|---|---|---|---|---|
| 1 | MW Markers (Cambrex | — | — | 5 μl |
| 2 | Non relevant protein | 20 | 10 | 30 |
| 3 | Non relevant protein | 20 | 10 | 30 |
| 4 | Non relevant protein | 20 | 10 | 30 |
| 5 | Non relevant protein | 20 | 10 | 30 |
| 6 | Non relevant protein | 20 | 10 | 30 |
| 7 | | | | |
| 8 | 71 MCP-1 99 A4 + A5 | 20 | 10 | 27 |
| 9 | 71 MCP-1 99 A6 | 20 | 10 | 27 |
| 10 | 71 MCP-1 99 D2 | 20 | 10 | 27 |

TABLE 10

SDS-PAGE of MCP-1-92

| Lane | SAMPLE | Sample Vol. | 3XS.B | Loading |
|---|---|---|---|---|
| 1 | MW Markers (Cambrex) | — | — | 10 |
| 2 | BSA 1 mg/ml | 20 | 10 | 28 |
| 3 | BSA 0.5 mg/ml | 20 | 10 | 28 |
| 4 | BSA 0.25 mg/ml | 20 | 10 | 28 |
| 5 | BSA 0.1 mg/ml | 20 | 10 | 28 |
| 6 | Non relevant protein | 20 | 10 | 14 |
| 7 | | | | |
| 8 | Non relevant protein | 20 | 10 | 14 |
| 9 | | | | |
| 10 | 224 MCP1 92-7ND bt1 A4- | 20 | 10 | 28 |

TABLE 11

SDS-PAGE of MCP-1-65 m-Fc

| Lane | SAMPLE | Sample Vol. | 3XS.B with DTT | Loading Vol. |
|---|---|---|---|---|
| 1 | BSA 1 mg/ml | 20 | 10 | 25 |
| 2 | BSA 0.5 mg/ml | 20 | 10 | 25 |
| 3 | BSA 0.25 mg/ml | 20 | 10 | 25 |
| 4 | BSA 0.1 mg/ml | 20 | 10 | 25 |
| 5 | Non relevant protein | 20 | 10 | 25 |
| 6 | MW Markers (Cambrex Prosieve) | — | — | 10 |
| 7 | Non relevant protein | 20 | 10 | 25 |
| 8 | | | | |
| 9 | 272 MCP 1 65 m Fc bt1 + BSA | 20 | 10 | 25 |
| 10 | | | | |
| 11 | Non relevant protein | 20 | 10 | 25 |

Example 4

Antagonistic Activity of MCP-1 Variants

This Example relates to functional testing of MCP-1 variants according to the present invention, produced as described above. As described in greater detail below, the MCP-1 variants according to the present invention inhibited THP-1 cell migration induced by MCP-1.

Materials and Methods

Briefly, the effect of MCP-1 variants according to the present invention on inhibition of MCP-1 induced cell migration was studied using the human monocytic cell line THP-1. A known MCP-1 mutein, MCP1-92-7ND (SEQ ID NO:13), which was previously shown to have an antagonistic activity in this cell line, was also produced and used as positive control. Cell migration was studied in a transwell system, in which MCP-1 (0.3 nM) was present in the lower chamber while the studied proteins were present both in the upper and the lower chambers at various concentrations (0.3-30 nM). Cells that migrated to the lower chamber were collected and counted by FACS.

600 μl of 0.3 nM MCP-1 in 0.1% BSA/RPMI (R&D; #279-MC) was added to the lower well of a transwell apparatus (Corning; cat: ca-3421 48/cs). The tested proteins were added either to the upper or to the lower wells, or to both wells. The THP-1 cells (ATCC; TIB-202) were washed in 0.1% BSA/RPMI, and then resuspended in 0.1% BSA/RPMI to a final concentration of $5 \times 10^6$ cells/ml. Then 100 μl of the suspended cells (150,000 cells/well) were transferred into the upper well of a transwell apparatus and incubated for 4 hours at 37° C. The upper well was removed and the cells that had migrated to the lower well were counted by FACS.

Results

Figure 6:
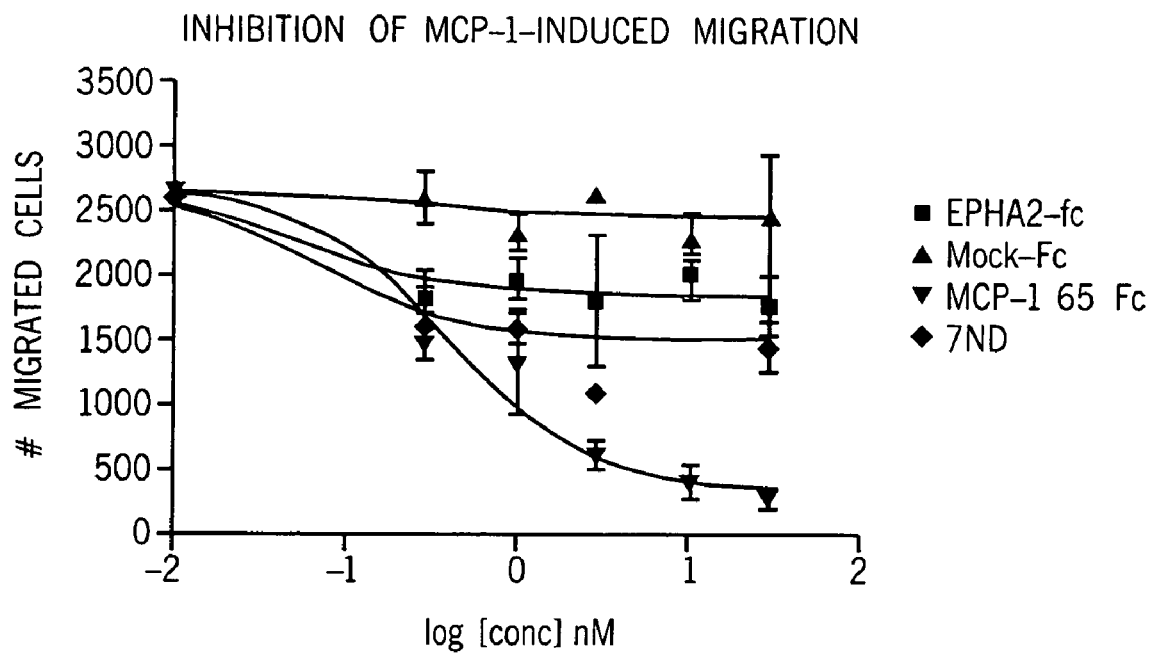
FIG. 6 demonstrates inhibition of MCP-1-induced THP-1 cell migration by MCP-1-65-Fc variant of the present invention (SEQ ID NO:15). The curve representing the MCP-1-65-Fc variant is marked with down-pointing triangles; the curve representing the mock-Fc is marked with up-pointing triangles; the curve representing the non-relevant EPHA2-Fc control is marked with squares; and the positive MCP-1-92-7ND (7ND control) curve is diamond shaped.

MCP-1 at 0.3 nM induced migration of about three-fold. FIG. 6 shows the effect of MCP-1-65-Fc variant of the present invention (SEQ ID NO:15) on MCP-1-induced migration. As can be seen in FIG. 6, MCP-1-65-Fc inhibited the cell migration by up to 90%, with an IC50 value of 0.4 nM, while the relevant mock showed no antagonistic activity. MCP-1-65-Fc was more active than the MCP-1 mutein positive control, MCP1-92-7ND.

As a control to the possible effect of the Fc on migration, a non-relevant Fc-fused protein (EphA2-Fc), as well as IgG1 antibodies, were also assessed. EphA2-Fc showed some inhibitory activity (~30%, FIG. 6) while IgG1 showed no inhibitory activity and was comparable to the inhibition obtained with the mock-Fc (data not shown). MCP-1-65-Fc was clearly far more active than either negative control.

Figure 7:
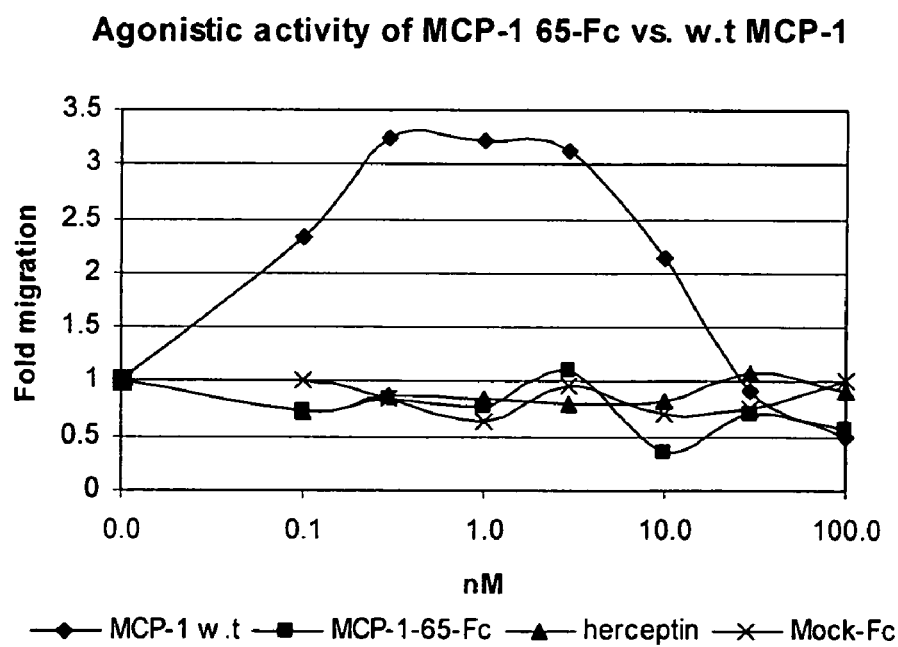
FIG. 7 demonstrates that MCP-1-65-Fc variant of the present invention (SEQ ID NO:15) has no agonistic activity on MCP-1-induced THP-1 cell migration. The curve representing the known MCP-1 (SEQ ID NO:8) is marked with diamond shapes; the curve representing the mock-Fc is X-marked; the curve representing the MCP-1-65-Fc variant is marked with squares; and the curve representing non-relevant herceptin control is marked with triangles.

MCP-1-65-Fc was also tested for agonistic (activating) activity in comparison to the commercial wild type MCP-1. As shown in FIG. 7, MCP-1-65-Fc has no agonistic activity in the concentration range that was effective in the antagonistic assay; even at higher concentrations, no agonistic activity is seen.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An isolated MCP-1 variant polypeptide comprising the amino acid sequence of SEQ ID NO: 9.

2. A pharmaceutical composition comprising the polypeptide of claim 1 and a pharmaceutically acceptable carrier.

3. An isolated MCP-1 variant polypeptide consisting of the amino acid sequence of SEQ ID NO: 9.

4. A pharmaceutical composition comprising the polypeptide of claim 3 and a pharmaceutically acceptable carrier.

* * * * *